(12) United States Patent
Seipel

(10) Patent No.: US 7,378,115 B2
(45) Date of Patent: May 27, 2008

(54) HERBAL COMPOSITIONS FOR THE PREVENTION OR TREATMENT OF URINARY INCONTINENCE AND OVERACTIVE BLADDER

(75) Inventor: Tracey Anne Seipel, Kelvin Grove (AU)

(73) Assignee: Biologic Health Solutions Pty Ltd. (AU)

( * ) Notice: Subject to any disclaimer, the term of this patent is extended or adjusted under 35 U.S.C. 154(b) by 302 days.

(21) Appl. No.: 11/206,324

(22) Filed: Aug. 18, 2005

(65) Prior Publication Data

US 2006/0040004 A1 Feb. 23, 2006

Related U.S. Application Data

(60) Provisional application No. 60/602,530, filed on Aug. 18, 2004.

(51) Int. Cl.
*A61K 36/00* (2006.01)

(52) U.S. Cl. ......................... 424/775; 424/779; 424/725

(58) Field of Classification Search ...................... None
See application file for complete search history.

(56) References Cited

U.S. PATENT DOCUMENTS

| | | | | |
|---|---|---|---|---|
| 5,683,991 | A * | 11/1997 | Guggenbichler et al. | 514/55 |
| 6,277,396 | B1 * | 8/2001 | Dente | 424/439 |
| 7,025,998 | B2 * | 4/2006 | Senin et al. | 424/757 |
| 2004/0147459 | A1 * | 7/2004 | Oneal et al. | 514/23 |
| 2004/0241260 | A1 * | 12/2004 | Senin et al. | 424/757 |

OTHER PUBLICATIONS

Castleman, M. The Healing Herbs—The Ultimate Guide to the Curative Power of Nature's Medicines. 1991. Rodale Press, Emmaus, PA, pp. 219-221.*
The PDR for Herbal Medicines. 1998. Medical Economics Co., Montvaile, NJ. pp. 830-831.*
Schauss et al. Faseb J. Mar. 2006. vol. 20, No. 5, Part 2, p. A990—Meeting Abstract. Biosis Abstract enclosed.*
Anderson, K.E., New parmacologic targets for the treatment of the overactive bladder: an update, Urology. 63(3 Suppl 1):32-41., 3A: 32-41 (2004).
Appell, R.A. et al., Pharmacokinetics, metabolism, and saliva output during transdermal and extended-release oral oxybutynin administration in healthy subjects, Mayo Clinical Proc., 78:696-702. (2003).
Arya, L.A. et al., Dietary caffeine intake and the risk for detrusor instability: a case-control study, Obstet Gynecol. 96(1):85-9 (2000).
Laycock, J., Association for Continence Advice, UK Survey of Patients-National Care Audit 1998-99, Aust. Continence J.; 6(2):15-23 (2000).
Battaglia, S., In: "The Complete Guide to Aromatherapy", The Perfect Potion Pty Ltd, Virginia, Brisbane, Qld, Australia, pp. 110-113, 116, 150-151, 158-159, 182-183, 184-185, 187 (1995).

Bone K., "Clinical Applications of Ayurvedic and Chinese Herbs. Monographs for the western herbal practitioner", Phyotherapy Press, Warwick, Qld. Australia, pp. 112-114 (1997).
Caddy, R., "Aromatherapy Essential Oils in Colour", Amberwood Publishing Ltd, East Horsley, Surrey, England; p. 14 (1997).
Chidell, L., "Aromatherapy. A Definitive Guide to Essential Oils" Hodder and Stoughton Ltd, Kent, UK, 23-24, 80-81 (1992).
Cruz, F., Mechanisms involved in new therapies for overactive bladder, Urology. 63(3 Suppl 1):65-73. (2004).
Damian, P.K., "Aromatherapy Scent and Psyche", Healing Arts Press, Rochester, Vermont, Canada, pp. 187-188 (1995).
Davis, P., "Aromatherapy An A-Z", The C. W. Daniel Company, Essex, England, p. 194 (1998).
Deshpande P. J. et al., *Crataeva nurvala* Hook and Forst (Varuna)—the Ayurvedic drug of choice in urinary disorders, Indian J. Med Res., 76(Suppl): 46-53(1982).
Geetha T. et al., Anti-inflammatory activity of lupeol and lupeol linoleate in rats. J Ethnopharmacol, 76(1):77-80 (2001).
Holmes, P., "The Energetics of Western Herbs", Artemis Press, Boulder, Colorado, USA, pp. 567-569, 792 (1989).
Lakshmi V. et al., A new pentacyclic triterpene from the root bark of *Crateva nurvala*. Planta Medica, 32: 214-216 (1977).
Lawless, J., "The Encyclopaedia of Essential Oils", (1992) Element Books for Jacaranda Wiley, Ltd, Australia, pp. 76-77, 88-89, 135-136 (1992).
Nadkarni K. M. et al., *Crataeva religiosa*, Indian Materia Medica. Bombay Popular Prakashan; British Herbal Pharmacopeia. Publ: British Herbal Medicine Association, pp. 387-388 (1983).
Nagao A. et al., Inhibition of xanthine oxidase by flavonoids, Biosci. Biotechnol. Biochem. 63(10): 1787-90 (1999).
Pathak A.S. et al., "Overactive Bladder: Drug therapy versus nerve stimulation", Nat. Clin. Pract. Urol., 2(7):310-311 (2005).
Price, S., "Practical Aromatherapy", Thorsons, Harper Collins Publishers, California, U.S., pp. 174-175 (1983).
Price, S., "The Aromatherapy Workbook", Thorsons (Harper Collins), California, USA, p. 66-7 (1993).
Salvat A. et al., Screening of some plants from Northern Argentina for their antimicrobial activity. Lett. Appl. Microbiol., 32(5):293-7 (2001).
Sellar, W., "The Directory of Essential Oils", Saffron Walden, The C. W. Daniel Company, Essex, England, 50-51, 106-107 (1992).
Sheppard-Hanger., "The Aromatherapy Practitioner Manual", Aquarius Publishing, Willetton, Western Australia, p. 183 (1995).
Steels E. et al., Herbal essential oils for urinary incontinence, Austr. Continence J., 7(2):34-37 (2001).
Steels E. et al., *Crataeva equisetum* reduce urinary incontinence symptoms, Austr. Continence J., 8(3): 46-50 (2002).

(Continued)

*Primary Examiner*—Christopher R. Tate
(74) *Attorney, Agent, or Firm*—Michel Morency; James F. Ewing; Foley & Lardner LLP

(57) ABSTRACT

The present invention relates to herbal compositions for the prevention or treatment of disorders of the urogenital system, e.g., urinary incontinence, enuresis (e.g., bed-wetting), benign prostatic hyperplasia, urinary calculi, cystitis, urinary tract infection, and overactive bladder. Specifically, the invention provides compositions that contain *C. nurvala* and *E. arvense* and methods of use thereof.

29 Claims, 12 Drawing Sheets

OTHER PUBLICATIONS

Stewart W.F. et al., Prevalence and burden of overactive bladder in the United States, World J. Urol. 20: 327-336, (2003).

Tisserand and Balacs, "Essential Oil Safety. A Guide for Health Care Professional", Churchill Livingstone, U. K.; pp. 28-29, 31, 33-34 (1995).

Valnet, J., "Practice of Aromatherapy", Saffron Walden, The C. W. Daniel Company, Essex, England, pp. 120-121 (1980).

Varalakshmi P. et al., Effect of *Crataeva nurvala* in experimental urolithiasis, J. Ethnopharmacol., 28: 313-321 (1990).

Varalakshmi P. et al., Effect of *Crataeva nurvala* on the biochemistry of the small intestinal tract of normal and stone-forming rats, J. Ethnopharmacol. 31: 67-73 (1991).

International Search Report, PCT/IB2005/003370, Mailed Mar. 14, 2006.

Andersson, Karl-Erik, "Drug therapy for urinary incontinence," Bailliére's Clinical Obstetrics and Gynaecology, vol. 14, No. 2, pp. 291-313, 2000 Harcourt Publishers, Ltd.

Grases, F., et al., Urolithiasis and Phytotherapy, International Urology and Nephrology 26 (5), pp. 507-511 (1994).

Owens, R. G., et al., Comparative Tolerability of Drug therapies Used to Treat Incontinence and Enuresis, Drug Safety Aug. 19, 1998 (2), 123-139, Adis International Limited.

Bryant, C. et al., A randomized trial of the effects of caffeine upon frequency, urgency and urge incontinence, Austr. Continence J., Abstracts from the 9th Annual Scientific Meeting of the Continence Foundation of Australia, Hobert, Tasmania, 6(4):8 (2000).

Chevallier, A., "The Encyclopedia of Medicinal Plants", (Horn V. and Weil, C., Eds.) Dorling Kindersley Ltd., London (1996).

D'Agostino, M. et al., Sterols from *Equisetum arvense*. Boll. Soc. Ital. Biol. Sper., 60(12):2241-5 (1984).

Das P. K. et al., Anti-Inflammatory and Anti-Arthritic Activity of *Crataeva nurvala* Buch-Ham (Varuna), J. Res. Ind. Med., 9:49 (1974).

Geetha, T. et al., Anticomplement activity of triterpenes from *Crataeva nurvala* stem bark in adjuvant arthritis in rats. Gen. Pharmacol., 32(4):495-7 (1999).

Karantanis, E. et al., "Electroacupuncture for refractory idiopathic detensor instability or sensory urgency", Austr. Continence J., Abstracts from the 9th Annual Scientific Meeting of the Continence Foundation of Australia, Hobert, Tasmania, 6(4):6-7 (2000).

Malini, M. M., et al., Effect of lupeol, a pentacyclic triterpene, on urinary enzymes in hyperoxaluric rats, Jpn J Med Sci Biol. 48(5-6): 211-20 (1995).

Peake, S. et al., "Part and parcel of being a woman": female urinary incontinence and constructions of control, Med Anthropol. Q, 13(3):267-85 (1999).

Perez Gutierrez, R. M. et al., Diuretic activity of Mexican equisetum. J. Ethnopharmacol. 14(2-3):269-272 (1985).

Robinson, D. et al., Relationship Between Patient Reports of Urinary Incontinence Symptoms and Quality of Life Measures, Obstetrics and Gynecology, 92:2, 224-8 (1998).

Sullivan, J. et al., Pharmacological management of incontinence. Eur. Urol. 36 Suppl 1:89-95 (1999).

Tapp, A. J. S. et al., The treatment of detrusor instability in post-menopausal women with oxybutynin chloride: a double blind placebo controlled study, Br. J. Obstet. Gynaecol., 97(6):521-6 (1990).

Wada, Y. et al., Comparison of the effects of various anticholinergic drugs on human isolated urinary bladder, Arch. Int. Pharmacodyn. Ther., 330(1):76-89 (1995).

Wein, A.J., Pharmacological agents for the treatment of urinary incontinence due to overactive bladder, Expert Opin. Investig. Drugs. 10(1):65-83. (2001) Ashley Publications.

Xu, H.X. et al., Activity of plant flavonoids against antibiotic-resistant bacteria, Phytother Res., 15(1):39-43 (2001).

Sheppard-Hanger, S. (Lysin, G., Watt, M., and Moyler, D., eds.); The Aromatherapy Chart; The Aromatherapy Practitioner Reference Manual, vol. 1, no page No., 1994, Aquarius Publishing, Leeming, WA.

Steels, E., et al.; *Crataeva* and *equisetum* Reduce Urinary Incontinence Symptoms; Australian Commerce Journal, Aug. 2002, 8(3):46-50, pp. 1-4.

\* cited by examiner

HERBAL COMPOSITIONS FOR THE PREVENTION OR TREATMENT OF URINARY INCONTINENCE AND OVERACTIVE BLADDER

FIELD OF THE INVENTION

The present invention relates to herbal compositions for the prevention or treatment of urinary incontinence and overactive bladder.

BACKGROUND OF THE INVENTION

The loss of bladder control is called urinary incontinence. It occurs when the bladder muscles contract or the muscles surrounding the urethra relax without warning. Although urinary incontinence is observed in people of all ages, this disorder is more prevalent in older people. The U.S. National Institute on the Aging estimates that at least 1 in 10 people aged 65 or older suffer form urinary incontinence. Likewise, incontinence is a common condition in Australia and throughout the world, affecting from 12% of 18 year old women and up to 50% of women in their 70's. Symptoms can range from mild leaking to uncontrollable wetting. Women are more likely than men to have incontinence.

While aging, per se, does not cause urinary incontinence, it can occur for many reasons. For example, urinary tract infections, vaginal infection or irritation, constipation, and certain medicines can cause bladder control problems that may last only a short time. Sometimes incontinence lasts longer. Chronic incontinence can be caused by, e.g., weak bladder muscles, overactive bladder muscles, blockage from an enlarged prostate, damage to nerves that control the bladder from diseases such as multiple sclerosis or Parkinson's disease, or diseases such as arthritis that can make walking painful and slow.

There are multiple types of urinary incontinence which include, e.g., stress incontinence, urge incontinence, overflow incontinence and functional incontinence. Stress incontinence happens when urine leaks during exercise, coughing, sneezing, laughing, lifting heavy objects, or other body movements that put pressure on the bladder. It is the most common type of bladder control problem in younger and middle-age women. In some cases, it is related to childbirth. It may also begin around the time of menopause. Urge incontinence happens when people can't hold their urine long enough to get to the toilet in time. Healthy people can have urge incontinence, but it is often found in people who have diabetes, stroke, Alzheimer's disease, Parkinson's disease, or multiple sclerosis. It is also sometimes an early sign of bladder cancer. Overflow incontinence happens when small amounts of urine leak from a bladder that is always full. A man can have trouble emptying his bladder if an enlarged prostate is blocking the urethra. Diabetes and spinal cord injury can also cause this type of incontinence. Functional incontinence happens in many older people who have normal bladder control. They just have a hard time getting to the toilet in time because of arthritis or other disorders that make moving quickly difficult.

The current medical treatment options for urinary incontinence include behavioral interventions, e.g., bladder control training, drug medications, devices, e.g., catheters, and surgical procedures. Current drug therapy includes anticholinergics (with antispasmodic effects, e.g., oxybutinin), smooth muscle relaxants (antispasmodics), tricyclic antidepressants (e.g., imipramine), alpha-adrenergic antagonists, alpha-adrenergic agonists (e.g., phenylpropanolamine), prostaglandin synthesis inhibitors, calcium channel blockers and others (Sullivan and Abrams, Eur. Urol., 36 Suppl 1:89-95 (1999); Andersson, Baillieres Best Pract. Res. Clin. Obstet. Gynaecol., 14(2):291-313 (2000); Owens and Karram, Drug Saf., 19(2):123-39 (1998); Wada et al., Arch. Int. Pharmacodyn Ther., 330(1):76-89 (1995)). Unfortunately, most drug treatments are associated with unpleasant side effects, and this impacts on patient compliance (Sullivan and Abrams, Eur. Urol., 36 Suppl 1:89-95 (1999); Andersson, Baillieres Best Pract. Res. Clin. Obstet. Gynaecol., 14(2): 291-313 (2000); Owens and Karram, Drug Saf., 19(2):123-39 (1998); Wada et al., Arch. Int. Pharmacodyn Ther., 330(1):76-89 (1995))2-5.

Acetylcholine is the primary excitatory neurotransmitter involved in bladder emptying. Certain drugs commonly prescribed for urinary incontinence, such as oxybutynin hydrochloride, inhibit the muscarinic action of acetylcholine on smooth muscle, producing a direct antispasmodic action. These drugs relax the detrusor muscle. Wada Y. et al., Arch. Int. Pharmacodyn. Ther., 330(1):76-89 (1995); Tapp A. J. S. et al., Brit. J. Obstetrics Gynecology, 97: 521-6 (1990). These medications also produce unwanted anticholinergic effects, such as dry mouth, blurred vision and constipation. Pathak A S, Aboseif S R. Overactive Bladder: Drug therapy versus nerve stimulation. Nat Clin Pract Urol, 2(7):310-311, 2005; Wein (2001). Natural therapies have also been investigated for this condition (Steels et al., Aust. Continence J., 7(2):34-37 (2001); Karantanis et al., Aust. Continence J., 6(4):6-7 (2000); Arya et al., Obstetrics and Gynecology, 96(1):85-89 (2000); Bryant et al., Aust. Continence J., 6(4):8 (2000)). In Ayurveda, *Crateva nurvala* is a drug highly regarded for its use in the management of uropathies (Nadkarni, Indian Materia Medica. Bombay Popular Prakashan). Western traditional treatments recommend the use of *Equisetum arvense* (British Herbal Pharmacopeia. Publ: British Herbal Medicine Association 1983). Isolated clinical studies conducted using herb-based natural therapies for urinary incontinence include *Crateva nurvala* herb, acupuncture and dietary intervention such as modification of dietary intake. Deshpande et al., Indian J. Med. Res. 76(supp): 46-53, 1982; Karantanis et al., Aust. Continence J., 6(4): 6-7, 2000; Arya et al., Obstetrics and Gynecology, 96(1): 87-89, 2000; Bryant et al., Aust. Continence J., 6(4): 8, 2000.

Overactive bladder (OAB) is a condition characterized by the sudden need to urinate. If that need results in the unintentional leakage of urine, the condition is called urge incontinence ("OAB wet"). Thus, urge incontinence falls within the general definition of OAB. OAB result from the sudden, involuntary contraction of the muscle in the wall of the urinary bladder. Approximately one-third of people with OAB also experience urge incontinence ("OAB wet"), while approximately two-thirds have OAB without urge incontinence ("OAB dry"). According to the National Overactive Bladder Evaluation, OAB affects 16.5% of the population, with 16.9% of women and 16.0% of men affected. Stewart et al., World J. Urol. 20: 327-336, (2003).

OAB, like urinary incontinence, is treated primarily with anticholinergic drugs (e.g., oxybutinin). These inhibit the neurotransmitter acetylcholine from attaching to the bladder muscle, and thereby reduce the frequency and intensity of contractions of the bladder. Unfortunately, adverse side effects of these drugs include dry mouth, dry eyes, constipation, and headache. Anderson, Urology, 3A: 32-41 (2004); Cruz, Urology. 3A: 65-73 (2004); Appell et al., Mayo Clinical Proc., 78:696-702. (2003).

There are currently no medications that specifically target incontinence symptoms without having side effects elsewhere in the body. There is a need for the identification of new herb-containing compositions for the prevention or treatment of urinary incontinence and overactive bladder.

BRIEF SUMMARY OF THE INVENTION

The present invention provides herbal compositions useful for the prevention or treatment of urinary incontinence. The herb-containing compositions of the invention can be formulated in a dry delivery system, liquid delivery system, or a controlled-release vehicle. The herb-containing compositions of the invention are formulated as oral dosage units which include a tablet; dry powder; capsule; and caplet. In one embodiment, the invention provides an herb-containing composition comprising: a *Crateva nurvala* (*C. nurvala*) stem/bark preparation present at a concentration at least about 3,000 mg dry weight equivalents per oral dosage unit; an *Equisetum arvense* (*E. arvense*) herb preparation at a concentration of at least about 1,500 mg dry weight equivalents per oral dosage unit; a phosphorous concentration of at least about 24.9 mg dry weight equivalents per oral dosage unit; a magnesium concentration of at least about 14.5 mg dry weight equivalents per oral dosage unit; and a calcium concentration of at least about 16.3 mg dry weight equivalents per oral dosage unit.

The *C. nurvala* stem/bark preparation is present at a concentration at least about 3,000 mg dry weight equivalents per oral dosage unit. That is, the starting material is 3,000 mg of *C. nurvala* dry stem/bark. This starting material is eventually concentrated during the manufacture process to a ratio of 10:1 which equates to 300 mg of *C. nurvala* preparation. Accordingly, 300 mg of *C. nurvala* stem/bark preparation (which is concentrated) is equivalent to 3,000 mg dry weight of *C. nurvala* stem/bark or 3,000 mg of *C. nurvala* dry stem/bark starting material.

The *E. arvense* herb preparation is present at a concentration of at least about 1,500 mg dry weight equivalents per oral dosage unit. That is, the starting material is 1.500 mg of *E. arvense* herb. This starting material is eventually concentrated during the manufacture process to a ratio of 4:1 or 5:1 which equates to 375 mg or 300 mg of *E. arvense* herb preparation. So, for example, 300 mg of *E. arvense* herb preparation (which is concentrated) is equivalent to 1,500 mg dry weight of *E. arvense* herb or 1,500 mg of *E. arvense* dry herb starting material. In one embodiment, the standardized *E. arvense* herb preparation is derived from the stem parts of the *E. arvense* herb, i.e., a standardized *E. arvense* stem extract preparation.

In certain aspects of the present invention, it has been determined that batch variation in the silicon content and/or flavonoid content expressed as isoquercetrin of *E. arvense* herb preparations can have negative effects on the biological activity of the composition of the present invention. This problem has been resolved by the present invention by providing *E. arvense* herb preparations with optimized, standardized silicon content and/or flavonoid content expressed as isoquercetrin. In one embodiment, the invention provides an herb-containing composition, comprising a *C. nurvala* stem/bark preparation and a standardized *E. arvense* herb preparation with a silicon content from about 3% to about 13% silicon based on total dry weight of the *E. arvense* preparation, wherein the herb-containing composition is formulated as an oral dosage unit. Accordingly, for 1,500 mg dry weight of *E. arvense* herb or 1,500 mg of *E. arvense* dry herb starting material, which produces 300 mg of *E. arvense* herb preparation (which is concentrated), a silicon content from about 3% to about 13% would represent approximately 9 to 39 mg silicon.

In one embodiment, the *C. nurvala* stem/bark preparation is present in the herb-containing composition at a concentration from about 1,000 mg to about 6,000 mg dry weight equivalents per oral dosage unit. In one embodiment, the *C. nurvala* stem/bark preparation is present in the herb-containing composition at a concentration from about 1,000 mg to about 4,000 mg dry weight equivalents per oral dosage unit. In one embodiment, the *C. nurvala* stem/bark preparation is present in the herb-containing composition at a concentration from about 2,500 mg to about 3,500 mg dry weight equivalents per oral dosage unit. In one embodiment, the standardized *E. arvense* preparation is present in the herb-containing composition at a concentration from about 1 mg to about 3,000 mg dry weight equivalents per oral dosage unit. In one embodiment, the standardized *E. arvense* preparation is present in the herb-containing composition at a concentration from about 500 mg to about 2,500 mg dry weight equivalents per oral dosage unit. In one embodiment, the standardized *E. arvense* preparation is present in the herb-containing composition at a concentration from about 1,000 mg to about 2,000 mg dry weight equivalents per oral dosage unit. In one embodiment, the standardized *E. arvense* preparation is present in the herb-containing composition at a concentration from about 1,300 mg to about 1,600 mg dry weight equivalents per oral dosage unit.

In another embodiment, the herb-containing composition further comprises anhydrous colloidal silica, wherein the total silicon content of the herb-containing composition is from about 10 mg dry weight equivalents to about 71 mg dry weight equivalents per oral dosage unit. In one embodiment, the herb-containing composition further comprises anhydrous colloidal silica, wherein the total silicon content of the herb-containing composition is from about 15 mg dry weight equivalents to about 45 mg dry weight equivalents per oral dosage unit. In one embodiment, the herb-containing composition further comprises anhydrous colloidal silica, wherein the total silicon content of the herb-containing composition is from about 28 mg dry weight equivalents to about 34 mg dry weight equivalents per oral dosage unit.

In one embodiment, the standardized *E. arvense* herb preparation further comprises a total flavonoid content from about 0.01% to about 3% total flavonoids based on the total dry weight of the *E. arvense* preparation, wherein the total flavonoid content is expressed as isoquercetrin. In one embodiment, the standardized *E. arvense* herb preparation further comprises a total flavonoid content from about 0.1% to about 2.5% total flavonoids based on the total dry weight of the *E. arvense* preparation and expressed as isoquercetrin. In one embodiment, the standardized *E. arvense* herb preparation further comprises a total flavonoid content from about 0.5% to about 1.5% total flavonoids based on the total dry weight of the *E. arvense* preparation, wherein the total flavonoid content is expressed as isoquercetrin. In one embodiment, the standardized *E. arvense* herb preparation further comprises a total flavonoid content from at least about 0.8% total flavonoids based on the total dry weight of the *E. arvense* preparation, wherein the total flavonoid content is expressed as isoquercetrin.

In one embodiment, the herb-containing composition further comprises phosphorous, wherein the phosphorous is present at a concentration from about 5 mg dry weight equivalents to about 60 mg dry weight equivalents per oral dosage unit. In one embodiment, the herb-containing composition further comprises phosphorous, wherein the phosphorous is present at a concentration from about 10 mg dry weight equivalents to about 50 mg dry weight equivalents per oral dosage unit. In one embodiment, the herb-containing composition, further comprises phosphorous, wherein the phosphorous is present at a concentration from about 20 mg dry weight equivalents to about 30 mg dry weight equivalents per oral dosage unit.

In one embodiment, the herb-containing composition further comprises calcium, wherein the calcium is present at a concentration from about 1 mg dry weight equivalents to about 30 mg dry weight equivalents per oral dosage unit. In one embodiment, the herb-containing composition of claim 1, further comprises calcium, wherein the calcium is present at a concentration from about 5 mg dry weight equivalents to about 25 mg dry weight equivalents per oral dosage unit. In one embodiment, the herb-containing composition, further comprises calcium, wherein the calcium is present at a concentration from about 10 mg dry weight equivalents to about 20 mg dry weight equivalents per oral dosage unit.

In one embodiment, the herb-containing composition of further comprising magnesium, wherein the magnesium is present at a concentration from about 1 mg dry weight equivalents to about 30 mg dry weight equivalents per oral dosage unit. In one embodiment, the herb-containing composition, further comprising magnesium, wherein the magnesium is present at a concentration from about 5 mg dry weight equivalents to about 25 mg dry weight equivalents per oral dosage unit. In one embodiment, the herb-containing composition, further comprising magnesium, wherein the magnesium is present at a concentration from about 10 mg dry weight equivalents to about 20 mg dry weight equivalents per oral dosage unit.

In one embodiment, the invention provides an herb-containing composition, comprising: a *C. nurvala* stem/bark preparation present at a concentration at least about 3,000 mg dry weight equivalents per oral dosage unit; a standardized *E. arvense* stem extract preparation with a silicon content at least about 3% silicon based on total dry weight of the *E. arvense* stem extract preparation, wherein the standardized *E. arvense* stem extract preparation is present at a concentration of at least about 1,500 mg dry weight equivalents per oral dosage unit; a total silicon concentration of at least about 32.5 mg dry weight equivalents per oral dosage unit; a phosphorous concentration of at least about 24.9 mg dry weight equivalents per oral dosage unit; a magnesium concentration of at least about 14.5 mg dry weight equivalents per oral dosage unit; and a calcium concentration of at least about 16.3 mg dry weight equivalents per oral dosage unit.

In another embodiment, the invention provides an herb-containing composition, comprising a *C. nurvala* stem/bark preparation and a standardized *E. arvense* herb preparation with a total flavonoid content from about 0.01% to about 3% total flavonoids based on the total dry weight of the *E. arvense* preparation, wherein the total flavonoid content is expressed as isoquercetrin and wherein the herb-containing composition is formulated as an oral dosage unit. In one embodiment, the standardized *E. arvense* herb preparation further comprises a total flavonoid content from about 0.1% to about 2.5% total flavonoids based on the total dry weight of the *E. arvense* preparation and expressed as isoquercetrin. In one embodiment, the standardized *E. arvense* herb preparation comprises a total flavonoid content from about 0.5% to about 1.5% total flavonoids based on the total dry weight of the *E. arvense* preparation, wherein the total flavonoid content is expressed as isoquercetrin. In one embodiment, the standardized *E. arvense* herb preparation comprises a total flavonoid content from at least about 0.8% total flavonoids based on the total dry weight of the *E. arvense* preparation, wherein the total flavonoid content is expressed as isoquercetrin.

In one embodiment, the invention provides a pharmaceutical composition comprising the herb-containing composition of the invention and a pharmaceutically-acceptable carrier.

In another aspect, the invention provides methods of preventing or treating a urogenital system disorder in a subject, by administering to the subject an herb-containing composition of the invention in an amount sufficient to prevent or treat the urogenital system disorder. In one embodiment, the urogenital system disorder is urinary incontinence; enuresis; benign prostatic hyperplasia; urinary calculi; cystitis; or a urinary tract infection.

BRIEF DESCRIPTION OF THE DRAWINGS

The invention will be more fully understood by reference to the following drawings which are for illustrative purposes only.

DETAILED DESCRIPTION OF THE INVENTION

Figure 1:
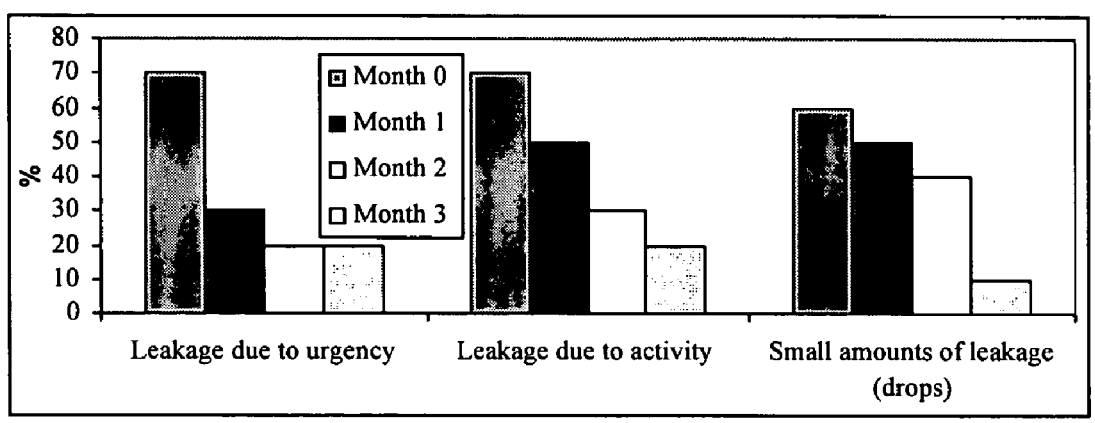
FIG. 1 is a histogram graph showing the percentage of "extremely bothered" responses during clinical assessment of an herb-based cream to treat urinary incontinence.

It is to be appreciated therefore that certain aspects, modes, embodiments, variations and features of the invention described below in various levels of detail in order to provide a substantial understanding of the present invention. In general, such disclosure provides beneficial herb-containing compositions, combinations of such compositions with other dietary supplement compositions, and related methods of producing and using same.

Accordingly, the various aspects of the present invention relate to therapeutic or prophylactic uses of certain particular herb-based compositions in order to prevent or treat a disease, injury or condition related to urinary incontinence. Accordingly, various particular embodiments that illustrate these aspects follow.

It is to be appreciated that the various modes of treatment or prevention of medical conditions as described are intended to mean "substantial", which includes total but also less than total treatment or prevention, and wherein some biologically or medically relevant result is achieved.

Definitions

A "subject," as used herein, is preferably a mammal, such as a human, but can also be an animal, e.g., domestic animals (e.g., dogs, cats and the like), farm animals (e.g., cows, sheep, pigs, horses and the like) and laboratory animals (e.g., rats, mice, guinea pigs and the like).

An "effective amount" of a composition, as used herein, is a quantity sufficient to achieve a desired therapeutic and/or prophylactic effect, for example, an amount which results in the prevention of or a decrease in the symptoms associated with a disease that is being treated. The amount of composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compositions of the present invention, sufficient for achieving a therapeutic or prophylactic effect.

It is advantageous to formulate oral compositions in dosage unit form for ease of administration and uniformity of dosage. Dosage unit form as used herein refers to physically discrete units suited as unitary dosages for the subject to be treated; each unit containing a predetermined quantity of active composition calculated to produce the desired therapeutic effect in association with the required pharmaceutical carrier. The specification for the dosage unit forms of the invention are dictated by and directly dependent on the unique characteristics of the dietary supplement and the particular therapeutic effect to be achieved, and the limitations inherent in the art of producing such an active composition for the treatment of individuals. The pharmaceutical compositions can be included in a container, pack, or dispenser together with instructions for administration. Typically, an oral dose is taken two-times to four-times daily, until symptom relief is apparent. The compositions of the present invention can also be administered in combination with each other, or with one or more additional therapeutic compositions.

*Crateva nurvala* is a moderate-sized tree attaining a height of over 15 meters; it is named after cratevas (Krateuas), a Greek naturalist and physician of the 1st Century B.C. Common throughout India, the much-branched tree with a head of glossy trifoliate leaves looks very majestic when in full bloom from March to May (earlier in the South). The bark of the tree is reported to be used as a demulcent, antipyretic, sedative, alterative and tonic.

*Equisetum arvense* (botanical synonyms and common names include, e.g., Horsetail; Shave-grass; Bottle-brush; Paddock-pipes; Dutch Rushes; Pewterwort; Shavegrass; pewterwort; bottlebrush; horsetail rush; paddock-pipes; Dutch rushes; mare's tail) is a European herb which grows in moist waste places throughout temperate regions of the world and is cultivated in Yugoslavia. This perennial plant is common to moist loamy or sandy soil all over North America and Eurasia. No other herb in the entire plant kingdom is so rich in silicon as is horsetail. *Equisetum* is used medicinally. The sterile stems are harvested in summer and dried. The barren stems are useful as medicine, appearing after the fruiting stems have died down, and are used in their entirety, cut off just above the root. The herb is used either fresh or dried, but is said to be most efficacious when fresh. A fluid extract is prepared from it. The ashes of the plant are also employed.

The references cited throughout this application are incorporated herein by reference in their entireties.

Herb-Containing Compositions of the Invention

The present invention provides herb-containing compositions useful in a method of prophylaxis or treatment of disorders of the urogenital system, e.g., urinary incontinence, enuresis (e.g., bed-wetting), benign prostatic hyperplasia, urinary calculi, cystitis, and urinary tract infection (hereinafter, "UTI"). Specifically, the invention identifies compositions that contain *C. nurvala* and *E. arvense* that are useful in the prevention and treatment of disorders of the urogenital system. In one embodiment of the invention, the herb-containing composition contains *C. nurvala* stem/bark extract and *E. arvense* herb.

In one embodiment of the invention, the herb-containing composition of the invention is an oral supplement included in a dry delivery system, e.g., tablet, dry powder, and dry meal replacement mixture. In another embodiment, the herb-containing composition of the invention is an oral supplement included in a liquid delivery system, e.g., capsule, caplet, or beverage. In another embodiment, the herb-containing composition of the invention is an oral supplement included in a controlled-release vehicle, e.g., tablet, caplet, and capsule.

In another embodiment, the herb-containing composition of the invention contains from about 1,000 mg to about 6,000 mg dry weight equivalents *C. nurvala* stem/bark extract per oral dosage unit. In another embodiment, the herb-containing composition of the invention contains from about 1,000 mg to about 4,000 mg dry weight equivalents *C. nurvala* stem/bark extract per oral dosage unit. In another embodiment, the herb-containing composition of the invention contains from about 2,500 mg to about 3,500 mg dry weight equivalents *C. nurvala* stem/bark extract per oral dosage unit. A *C. nurvala* stem/bark extract is an extract prepared using both the stem parts and bark of the *C. nurvala* herb.

In another embodiment, the herb-containing composition of the invention contains from about 1,000 mg to about 6,000 mg dry weight equivalents *C. nurvala* stem extract per oral dosage unit. In another embodiment, the herb-containing composition of the invention contains from about 1,000 mg to about 4,000 mg dry weight equivalents *C. nurvala* stem extract per oral dosage unit. In another embodiment, the herb-containing composition of the invention contains from about 2,500 mg to about 3,500 mg dry weight equivalents *C. nurvala* stem extract per oral dosage unit.

In another embodiment, the herb-containing composition of the invention contains from about 1,000 mg to about 6,000 mg dry weight equivalents *C. nurvala* bark extract per oral dosage unit. In another embodiment, the herb-containing composition of the invention contains from about 1,000 mg to about 4,000 mg dry weight equivalents *C. nurvala* bark extract per oral dosage unit. In another embodiment, the herb-containing composition of the invention contains from about 2,500 mg to about 3,500 mg dry weight equivalents *C. nurvala* bark extract per oral dosage unit.

To prepare the herb-containing composition of the invention, the bark and stems of *C. nurvala* were isolated from the rest the *C. nurvala* plant and dried. The dried bark and stems of *C. nurvala* were extracted using 70% Ethanol/Water. The liquid extract was then concentrated to a ratio of 10:1. Maltodextrin was used as an excipient. The final product, i.e., *C. nurvala* stem/bark extract, used in the herb-containing composition of the invention was a brown to dark brown powder.

In another embodiment of the invention, the *E. arvense* herb preparation component of the herb-containing composition of the invention is derived from the leaf of the *E. arvense* herb. In one embodiment of the invention, the *E. arvense* herb preparation component of the herb-containing composition of the invention is derived from the stem of the

*E. arvense* herb. In another embodiment of the invention, the *E. arvense* herb preparation component of the herb-containing composition of the invention is derived from a mixture of plant parts of the *E. arvense* herb. In another embodiment of the invention, the *E. arvense* herb preparation component of the herb-containing composition of the invention is derived from all the parts of the plant that extend aboveground. In one embodiment, the herb-containing composition of the invention contains from about 1 mg to about 3,000 mg dry weight equivalents *E. arvense* herb preparation per oral dosage unit. In another embodiment, the herb-containing composition of the invention contains from about 500 mg to about 2,500 mg dry weight equivalents *E. arvense* herb preparation per oral dosage unit. In another embodiment, the herb-containing composition of the invention contains from about 1,000 mg to about 2,000 mg dry weight equivalents *E. arvense* herb preparation per oral dosage unit. In another embodiment, the herb-containing composition of the invention contains from about 1,300 mg to about 1,600 mg dry weight equivalents *E. arvense* herb preparation per oral dosage unit.

Silicon has been identified as a contributor to the biological activity of *E. arvense* herb. Non-standardized preparations of *E. arvense* herb generally contain silicon from about 1.2% to about 6.9% silicon based on total dry weight of preparation. In one aspect of the present invention, it has been determined that batch variation in the silicon content of *E. arvense* herb preparations can have negative effects on the biological activity of the composition of the present invention. This problem has been resolved by the present invention by providing an *E. arvense* herb preparation with optimized, standardized silicon content. Accordingly, in one embodiment of the invention, the silicon content of the *E. arvense* herb preparation in the herb-containing preparation of the invention is standardized. The use of a standardized preparation *E. arvense* herb is advantageous because the inter-batch variation of silicon is reduced, thus the composition of the present invention yields more consistent preventative or therapeutic effect. In one embodiment, the *E. arvense* herb preparation is standardized to contain from about 3% silicon to about 13% silicon based on the total dry weight of the *E. arvense* herb preparation. In another embodiment, the *E. arvense* herb preparation is standardized to contain from about 5% silicon to about 10% silicon based on the total dry weight of the *E. arvense* herb preparation. In another embodiment, the *E. arvense* herb preparation is standardized to contain at least about 6% silicon based on the total dry weight of the *E. arvense* herb preparation.

In addition to silicon, *E. arvense* contains about 5 percent of a saponin, designated equisetonin, and several flavone glycosides (a.k.a., flavonoids) including isoquercetrin, galuteolin, and equisetrin. Isoquercetrin (a.k.a, isoquercitrin; Quercetin 3-O-β-D-glucopyranoside; 4H-1-Benzopyran-4-one, 2-(3,4-dihydroxy-phenyl)-3-(β-D-glucofuranosyloxy)-5,7-dihydroxy-). Flavonoids, e.g., isoquercetrin, may have important pharmacological properties. Many flavonoids are diuretic, some are antispasmodic, anti-inflammatory, antiseptic and even antitumor. However, the predominant action of the flavonoids as a group is on the vascular system. The flavone glycosides and the saponin likely combine to account for the diuretic action of *E. arvense*.

In another aspect of the present invention, it has been determined that batch variation in the total flavonoid content (expressed as isoquercetrin content) of *E. arvense* herb preparations can have negative effects on the biological activity of the composition of the present invention. This problem has been resolved by the present invention by providing an *E. arvense* herb preparation with optimized, standardized total flavonoid content (expressed as isoquercetrin content). Accordingly, in one embodiment of the invention, the total flavonoid content (expressed as isoquercetrin content) of the *E. arvense* herb preparation in the herb-containing preparation of the invention is standardized. The use of a standardized preparation *E. arvense* herb is advantageous because the inter-batch variation of total flavonoid content (expressed as isoquercetrin content) is reduced, thus the composition of the present invention yields more consistent preventative or therapeutic effect. In one embodiment, the *E. arvense* herb preparation is standardized to contain from about 0.01% flavonoids to about 3% flavonoids based on the total dry weight of the *E. arvense* herb preparation, wherein the total flavonoids are expressed as isoquercetrin equivalents. In another embodiment, the *E. arvense* herb preparation is standardized to contain from about 0.1% flavonoids to about 2.5% flavonoids based on the total dry weight of the *E. arvense* herb preparation, wherein the total flavonoids are expressed as isoquercetrin equivalents. In another embodiment, the *E. arvense* herb preparation is standardized to contain from about 0.5% flavonoids to about 1.5% flavonoids based on the total dry weight of the *E. arvense* herb preparation, wherein the total flavonoids are expressed as isoquercetrin equivalents. In another embodiment, the *E. arvense* herb preparation is standardized to contain at least about 0.8% flavonoids based on the total dry weight of the *E. arvense* herb preparation, wherein the total flavonoids are expressed as isoquercetrin equivalents.

In one embodiment, the *E. arvense* herb preparation is standardized to organic silicon content by a solvent extraction process using raw material with a silicon content that met a minimum silicon requirement, e.g., 3% silicon. In one embodiment, the *E. arvense* herb preparation of the herb-containing composition of the invention is derived from the stems of the *E. arvense* herb and standardized for silica content, i.e., *E. arvense* stem extract preparation. Briefly, stem parts of the *E. arvense* herb were removed from the plant and dried. They were then measured for a minimum of 2.5% silicon content via HPLC analysis before being accepted for the extraction process. An extract was obtained using 65% (v/v) ethanol/water extraction solvent. The extract was concentrated to a ratio of approximately 4:1. The extract was then tested again for minimum 3% silicon content via HPLC. The final extract dry concentrate appeared as a fine brown powder with a characteristic odor and taste.

In another embodiment, the *E. arvense* herb preparation is standardized to organic silicon by a solvent extraction process. Briefly, stem parts of the *E. arvense* herb were removed from the plant and dried. Morphological examination of the starting biomass (this includes both microscopic and macroscopic characteristics) ensured the correct species is being used (e.g., an authenticated voucher specimen was stored on file for species identification). An extract was obtained using hot water (between about 50° C. and about 100° C.) as a solvent. The extract was concentrated to a ratio of approximately 5:1. The extract was then dried. The extract was tested for a minimum of approximately 3% silicon content via UV-Vis Spectrophotometry (silicon dioxide is used as a reference substance). If the extract fell outside the desired standards above, it was titrated with a dried extract that had undergone the same process as above. The final extract dry concentrate appeared as a yellow-brown colored powder.

In one embodiment, the *E. arvense* herb preparation of the herb-containing composition of the invention is derived from the stems of the *E. arvense* herb and standardized for total flavonoid content, i.e., *E. arvense* stem extract preparation.

In another embodiment, the *E. arvense* herb preparation is standardized to flavonoid (expressed as isoquercetrin) content by a solvent extraction process. Briefly, stem parts of the *E. arvense* herb were removed from the plant and dried. They were then identified by TLC. (isoquercetrin is used as reference substance). Morphological examination of the starting biomass (this included both microscopic and macroscopic characteristics) ensured the correct species was being used (e.g., an authenticated voucher specimen was stored on file for species identification). An extract was obtained using hot water (between about 50° C. and about 100° C.) as a solvent. The extract was concentrated to a ratio of approximately 5:1. The extract was then dried. The extract was tested for a minimum of approximately 0.01%.isoquercetrin via UV-Vis Spectrophotometry (isoquercetrin was used as reference substance). If the extract fell outside the desired standards above, it was titrated with a dried extract that had undergone the same process as above. The final extract dry concentrate appeared as a yellow-brown colored powder.

In one embodiment, the *E. arvense* herb preparation was standardized to organic silicon content and flavonoid content (expressed as isoquercetrin) using the methods described above.

In one aspect of the present invention, the herb-containing composition of the invention contains *C. nurvala* stem/bark extract and *E. arvense* herb preparation and colloidal anhydrous silica. The additional silicon assists with urogenital tissue support, strengthening and firmness. In one embodiment, the herb-containing composition of the invention contains from about 10 mg dry weight equivalents to about 71 mg dry weight equivalents of total silicon per oral dosage unit. In another embodiment, the herb-containing composition of the invention contains from about 15 mg dry weight equivalents to about 45 mg dry weight equivalents of total silicon per oral dosage unit. In another embodiment, the herb-containing composition of the invention contains from about 28 mg dry weight equivalents to about 34 mg dry weight equivalents of total silicon per oral dosage unit.

In another aspect of the invention, the herb-containing composition of the invention contains phosphorous. In one embodiment, the herb-containing composition of the invention contains from about 5 mg dry weight equivalents of phosphorous to about 60 mg dry weight equivalents of phosphorous per oral dosage unit. In another embodiment, the herb-containing composition of the invention contains from about 10 mg dry weight equivalents of phosphorous to about 50 mg dry weight equivalents of phosphorous per oral dosage unit. In another embodiment, the herb-containing composition of the invention contains from about 20 mg dry weight equivalents of phosphorous to about 30 mg dry weight equivalents of phosphorous per oral dosage unit.

In another aspect of the invention, the herb-containing composition of the invention contains calcium. In one embodiment, the herb-containing composition of the invention contains from about 1 mg dry weight equivalents of calcium to about 30 mg dry weight equivalents of calcium per oral dosage unit. In another embodiment, the herb-containing composition of the invention contains from about 5 mg dry weight equivalents of calcium to about 25 mg dry weight equivalents of calcium per oral dosage unit. In another embodiment, the herb-containing composition of the invention contains from about 10 mg dry weight equivalents of calcium to about 20 mg dry weight equivalents of calcium per oral dosage unit.

In another aspect of the invention, the herb-containing composition of the invention contains magnesium. In one embodiment, the herb-containing composition of the invention contains from about 1 mg dry weight equivalents of magnesium to about 30 mg dry weight equivalents of magnesium per oral dosage unit. In another embodiment, the herb-containing composition of the invention contains from about 5 mg dry weight equivalents of magnesium to about 25 mg dry weight equivalents of magnesium per oral dosage unit. In another embodiment, the herb-containing composition of the invention contains from about 10 mg dry weight equivalents of magnesium to about 20 mg dry weight equivalents of magnesium per oral dosage unit.

In another embodiment, the herb-containing composition of the invention is used in a cream. In one embodiment, the herb-containing composition of the invention contains from about 1 mg to about 100 mg dry weight equivalents *C. nurvala* stem/bark extract per gram of cream. In another embodiment, the herb-containing composition of the invention contains from about 10 mg to about 60 mg dry weight equivalents *C. nurvala* stem/bark extract per gram of cream. In another embodiment, the herb-containing composition of the invention contains from about 40 mg to about 60 mg dry weight equivalents *C. nurvala* stem/bark extract per gram of cream.

In another embodiment, the herb-containing composition of the invention contains from about 1 mg to about 60 mg dry weight equivalents *E. arvense* herb per gram of cream. In another embodiment, the herb-containing composition of the invention contains from about 5 mg to about 40 mg dry weight equivalents *E. arvense* herb per gram of cream. In another embodiment, the herb-containing composition of the invention contains from about 10 mg to about 30 mg dry weight equivalents *E. arvense* herb per gram of cream.

In another embodiment of the invention, the herb-containing composition contains orange oil. In one embodiment, the herb-containing composition of the invention contains from about 1 mg to about 30 mg orange oil per gram of cream. In another embodiment, the herb-containing composition of the invention contains from about 5 mg to about 25 mg dry orange oil per gram of cream. In another embodiment, the herb-containing composition of the invention contains from about 8 mg to about 12 mg orange oil per gram of cream.

In one embodiment of the invention, the herb-containing composition contains *Juniperus virginiana* (Cedarwood) stem essential oil. In one embodiment, the herb-containing composition of the invention contains from about 1 µg to about 1,000 µg *J. virginiana* stem essential oil per gram of cream. In another embodiment, the herb-containing composition of the invention contains from about from about 250 µg to about 750 µg *J. virginiana* stem essential oil per gram of cream. In another embodiment, the herb-containing composition of the invention contains from about 400 µg to about 600 µg *J. virginiana* stem essential oil per gram of cream.

In one embodiment of the invention, the herb-containing composition contains Myrrh oil. In one embodiment, the herb-containing composition of the invention contains from about 1 µg to about 1,000 µg Myrrh oil per gram of cream. In another embodiment, the herb-containing composition of the invention contains from about from about 250 µg to about 750 µg Myrrh oil per gram of cream. In another embodiment, the herb-containing composition of the invention contains from about 400 μg to about 600 μg Myrrh oil per gram of cream.

In one embodiment of the invention, the herb-containing composition contains Orange flower oil. In one embodiment, the herb-containing composition of the invention contains from about 1 μg to about 1,000 μg Orange flower oil per gram of cream. In another embodiment, the herb-containing composition of the invention contains from about from about 250 μg to about 750 μg Orange flower oil per gram of cream. In another embodiment, the herb-containing composition of the invention contains from about 400 μg to about 600 μg Orange flower oil per gram of cream.

In one embodiment of the invention, the herb-containing composition contains *Cupressus sempervirens* (Cypress) leaf oil. In one embodiment, the herb-containing composition of the invention contains from about 1 μg to about 1,000 μg *C. sempervirens* leaf oil per gram of cream. In another embodiment, the herb-containing composition of the invention contains from about from about 50 μg to about 500 μg *C. sempervirens* leaf oil per gram of cream. In another embodiment, the herb-containing composition of the invention contains from about 75 μg to about 125 μg *C. sempervirens* leaf oil per gram of cream.

In another embodiment of the invention, the herb-containing composition contains d-alpha-tocopheryl acetate (Natural Vitamin E). In one embodiment of the invention the herb-containing composition of the invention contains d-alpha-tocopheryl acetate. In one embodiment, the herb-containing composition of the invention contains from about 0.1 mg to about 25 mg d-alpha-tocopheryl acetate per gram of cream. In another embodiment, the herb-containing composition of the invention contains from about 1 mg to about 10 mg dry d-alpha-tocopheryl acetate per gram of cream. In another embodiment, the herb-containing composition of the invention contains from about 4 mg to about 6 mg d-alpha-tocopheryl acetate per gram of cream.

In another embodiment of the invention, the herb-containing composition contains diazolidinylurea. In one embodiment of the invention, the herb-containing composition of the invention contains diazolidinylurea. In one embodiment, the herb-containing composition of the invention contains from about 0.1 mg to about 10 mg diazolidinylurea per gram of cream. In another embodiment, the herb-containing composition of the invention contains from about 1 mg to about 5 mg dry diazolidinylurea per gram of cream. In another embodiment, the herb-containing composition of the invention contains from about 3 mg to about 3.5 mg diazolidinylurea per gram of cream.

In another embodiment of the invention, the herb-containing composition contains hydroxybenzoates. In one embodiment, the herb-containing composition of the invention contains hydroxybenzoates. In one embodiment, the herb-containing composition of the invention contains from about 0.1 mg to about 5 mg hydroxybenzoates per gram of cream. In another embodiment, the herb-containing composition of the invention contains from about 0.5 mg to about 3 mg dry hydroxybenzoates per gram of cream. In another embodiment, the herb-containing composition of the invention contains from about 1 mg to about 2 mg hydroxybenzoates per gram of cream.

In another embodiment of the invention, the herb-containing composition contains extracts of *C. nurvala* stem/bark extract; and *E. arvense* leaf; Orange oil; *J. virginiana* stem; Myrrh oil; Orange flower oil; *C. sempervirens* leaf; d-alpha-tocopheryl acetate; diazolidinylurea; and hydroxybenzoates.

Medicinal Properties and Uses of Compositions of the Invention

The present invention provides herb-containing compositions useful in a method of prophylaxis or treatment of disorders of the urogenital system, e.g., urinary incontinence, enuresis (e.g., bed-wetting), benign prostatic hyperplasia, urinary calculi, cystitis, and UTIs. It is thought that the primary active ingredients present in both the *Crateva* and *Equisetum* are the saponins and plant sterols. *Crateva* contains flavonoids, glucosinolates and the plant sterol, lupeol, while Equisetum contains the mineral, silica, flavonoids (isoquercetin, luteolin, and kaempferol) and the saponin, equisetin. Nadkarni K. M. et al., Indian Materia. Medica. Bombay Popular Prakashan; British Herbal Pharmacopeia. Publ: British Herbal Medicine Association 1983; Bone K. *Clinical Applications of Ayurvedic and Chinese Herbs. Monographs for the western herbal practitioner*. Phytotherapy Press, Warwick, Qld, Australia 1997; The German Commission E Monographs, 1998; D'Agostino M. et al., Boll. Soc. Ital. Biol. Sper., 30;60(12):2241-5 (1984); Pengelly A. *The constituents of medicinal plants: an introduction to the chemistry and therapeutics of herbal medicine*. Sunflower Herbal $2^{nd}$ Edition, Merriwa, NSW, Australia, 1996; Lakshmi V. et al., Planta Medica, 32: 214-216 (1977).

The herb-containing compositions of the present invention are useful in the prevention and treatment of urinary calculi. *Crateva* and *Equisetum* have been shown to alter urinary electrolytes in such a way so as to reduce lithogenic potentiality. Varalakshmi P et al., J. Ethnopharmacology, 28: 313-321 (1990); Anand R. et al., Indian J. Pharmacology, 27: 265-268 (1995); Grases F. et al., Int. Urol. Nephrol., 26(5): 507-511 (1994). *Crateva* has also been found to inhibit small intestinal Na-K-ATPase. Varalakshmi P. et al., J. Ethnopharmacology, 31: 67-73 (1991). These effects may be due primarily to the presence of the sterol lupeol. A number of studies have shown that lupeol has anti-oxaluric and anti-calcuric effects leading to increased spontaneous passing of stones and symptomatic relief. Varalakshmi P et al., J. Ethnopharmacology, 28: 313-321 (1990); Anand R. et al., Indian J. Pharmacology, 27: 265-268 (1995); Malini M. M., et al, Jpn. J. Med. Sci. Biol., 48(5-6):211-20 (1995); Lakshmi V. et al., Planta Medica, 32: 214-216 (1977).

It has been hypothesized that this passage of the stone may be produced via a tonic contractile action of the drug on the smooth muscle. Varalakshmi P et al., J. Ethnopharmacology, 28: 313-321 (1990); Anand R. et al., Indian J. Pharmacology, 27: 265-268 (1995); Deshpande P. J. et al., Indian J. Med. Res., 76(Suppl): 46-53 (1982). *Equisetum* may also assist with incontinence via a similar mechanism. Kaempferol, luteolin and isoquercetin, found in Equisetum are documented to inhibit xanthine oxidase and subsequent urate calculi formation. Nagao A. et al., Biosci. Biotechnol. Biochem., 63(10):1787-90 (1999). These herbal drugs act to improve the tone of the bladder wall. In 1982, Deshpande et al. reported that *Crateva* has beneficial effects on neurogenic bladder and post-prostatectomic atony of the bladder. Deshpande P. J. et al., Indian J. Med. Res., 76(Suppl):46-53 (1982).

The herb-containing compositions of the present invention are useful in the prevention and treatment of incontinence and benign prostatic hypertrophy and urinary incontinence. *Crateva* administration produces a marked relief of symptoms of frequency, incontinence, pain and retention of urine in men with hypotonic bladder as a result of benign prostatic hypertrophy. Deshpande P. J. et al., Indian J. Med. Res., 76 (Suppl):46-53 (1982). Crateva acts to increase the tone of the bladder and the expulsive force of urine, thereby helping effective evacuation. Deshpande P. J. et al., Indian J. Med. Res., 76 (Suppl):46-53 (1982). Cystometric studies analyzed in this paper also show that *Crateva* normalizes the tone of the urinary bladder and significantly decreases residual urine volume. The herb-containing compositions of the present invention, therefore, are useful in the prevention and treatment of urinary incontinence.

These results are also supported by animal studies where *Crateva* has been shown to increase the tone of both smooth and skeletal muscle in vitro. Das P. K. et al., J. Res. Ind. Med., 9:49 (1974). Animal studies show that 40 days of treatment with *Crateva* resulted in hypertonic curves of the urinary bladder when compared to initial curves. Das P. K. et al., J. Res. Ind. Med., 9:49 (1974).

*Equisetum* is rich in silicic acid and silicates. Silica supports the regeneration of connective tissue. Chevallier, A., *The Encyclopedia of Medicinal Plants*, (Horn V. and Weil, C., Eds.) Dorling Kindersley Ltd., London (1996). The present invention provides herb-containing compositions useful, therefore in the prophylaxis or treatment of disorders of the urogenital system, e.g., urinary incontinence, enuresis (e.g., bed-wetting), benign prostatic hyperplasia, urinary calculi, cystitis, and UTIs.

The herb-containing compositions of the present invention are useful in the prevention and treatment of UTIs and cystitis. It has been shown in rat studies that some species of the *Equisetum* family have a diuretic action, shown by excretion of sodium, potassium and chloride, similar to that of other drugs such as hydrochlorothiazide. Perez Gutierrez R. M. et al., J. Ethnopharmacol., 14(2-3):269-272 (1985); D'Agostino M. et al., Boll. Soc. Ital. Biol. Sper., 60(12): 2241-5 (1984). A more recent study using rats also demonstrated beneficial affects of the drugs in urolithiasis. Grases F. et al., Int. Urol. Nephrol., 26(5):507-511 (1994). These authors suggest that this result could be due to the antibacterial action of the constituents, namely, the saponins. Interestingly, *Crateva* has anti-inflammatory and antibacterial properties. Nadkarni K. M. et al., Indian Materia Medica. Bombay Popular Prakashan; Bone K. *Clinical Applications of Ayurvedic and Chinese Herbs. Monographs for the western herbal practitioner*. Phytotherapy Press, Warwick, Qld, Australia 1997; Salvat A. et al., Lett. Appl. Microbiology, 32(5): 293-7 (2001); Xu HX et al., Phytother. Res., 15(1): 39-43 (2001); Geetha T. et al., Gen. Pharmacol., 32(4):495-7 (1999); Geetha T. et al., J. Ethnopharmacol., 76(1):77-80 (2001). Combined with *Crateva's* tonic effects on smooth muscle, it is considered to assist with bladder evacuation, thereby decreasing residual urine, a known to contributing factor to UTIs. Deshpande P. J. et al., Indian J. Med. Res., 76(Suppl):46-53 (1982).

Isoquercetin, found in *Equisetum*, is known to have anti-inflammatory effects via inhibition of inflammatory prostaglandins, although *Crateva* is thought to produce anti-inflammatory effects via a different mechanism. D'Agostino M. et al., Boll. Soc. Ital. Biol. Sper., 30;60(12): 2241-5 (1984); Geetha T. et al., Gen. Pharmacol., 32(4): 495-7 (1999). The positive effect on chronic urinary tract infections is most likely a combination of anti-bacterial and anti-inflammatory actions.

The herb-containing compositions of the present invention are useful in the prevention and treatment of urinary incontinence, UTIs and enuresis. There is evidence for the use of Virginia cedarwood in treating incontinence, enuresis and assisting bladder tone as well as bladder infections, difficult urination and cystitis. Tisserand and Balacs, *Essential Oil Safety. A Guide for Health Care Professionals*. Churchill Livingstone, U. K., 1995; 28-29, 31, 33-34; Price, S. *Practical Aromatherapy*. Thorsons, Harper Collins Publishers, California, U.S., 1983; 157-8, 170-171, 174, 185; Davis, P. *Aromatherapy An A-Z*. The C. W. Daniel Company, Essex, England, 1998; 194; Valnet, J. *The Practice of Aromatherapy*. Saffron Walden, The C. W. Daniel Company, Essex, England, 1980; 120-121; Price, S. *The Aromatherapy Workbook*. Thorsons (Harper Collins), California, USA, 1993; 67; Caddy, R., *Aromatherapy Essential Oils in Colour*. Amberwood Publishing Ltd, East Horsley, Surrey, England, 1997; 14. The documented properties likely to produce this effect are the antispasmodic, diuretic, antiseptic and astringent.

Cypress is documented as an antispasmodic, astringent, antiseptic, deodorant, diuretic and tonic that may promote venous circulation to the kidneys and bladder area, improve bladder tone and assist with urinary incontinence and enuresis. Tisserand and Balacs, *Essential Oil Safety. A Guide for Health Care Professionals*. Churchill Livingstone, U. K., 1995; 28-29, 31, 33-34; Valnet, J. *The Practice of Aromatherapy*. Saffron Walden, The C. W. Daniel Company, Essex, England, 1980; 120-121, Holmes, P. *The Energetics of Western Herbs*. Artemis Press, Boulder, Color., USA, 1989; 567-569, 792; Damian, P & K. *Aromatherapy Scent and Psyche*. Healing Arts Press, Rochester, Vermont, Canada, 1995; 187-188; Price, S. *The Aromatherapy Workbook*. Thorsons (Harper Collins), California, USA, 1993; 67; Chidell, L. *Aromatherapy. A Definitive Guide to Essential Oils*. Hodder and Stoughton Ltd, Kent, UK, 1992; 23-24, 80-81; Keller, E. *The Compete Home Guide to Aromatherapy*. H J Kramer, Inc, Tiburon, Calif., USA, 1991; 178-179.

Recent literature describes Myrrh as an astringent and antiseptic that produces a soothing effect on mucous membranes of the urinary system and promotes healing of tissues. Battaglia, S. *The Complete Guide to Aromatherapy*. The Perfect Potion Pty Ltd, Virginia, Brisbane, Qld, Australia, 1995; 110-113, 116, 150-151, 158-159, 182-183, 184-185, 187; Lawless, J. *The Encyclopaedia of Essential Oils*. (1992) Element Books for Jacaranda Wiley, Ltd, Australia, 1992; 76-77, 88-89, 135-136. Orange and Neroli are documented as having anti-spasmodic, antiseptic and deodorant effects. 6,10; Sheppard-Hanger. *The Aromatherapy Practitioner Manual*. Aquarius Publishing, Willetton, Western Australia, 1995; 183; Sellar, W. *The Directory of Essential Oils*. Saffron Walden, The C. W. Daniel Company, Essex, England, 1992; 50-51, 106-107; Keller, E. *The Compete Home Guide to Aromatherapy*. H J Kramer, Inc, Tiburon, Calif., USA, 1991; 178-179.

The herb-containing compositions of the present invention are useful in the prevention and treatment of disorders of the prostate, e.g., benign prostatic hyperplasia. Essential oils are also recommended for male reproductive health, indicating a possible effect on the prostate in men. Battaglia, S. *The Complete Guide to Aromatherapy*. The Perfect Potion Pty Ltd, Virginia, Brisbane, Qld, Australia, 1995; 110-113, 116, 150-151, 158-159, 182-183, 184-185, 187; Price, S. *Practical Aromatherapy*. Thorsons, Harper Collins Publishers, California, U.S., 1983; 157-8, 170-171, 174, 185; Lawless, J. *The Encyclopaedia of Essential Oils*. (1992) Element Books for Jacaranda Wiley, Ltd, Australia, 1992; 76-77, 88-89, 135-136; Valnet, J. *The Practice of Aromatherapy*. Saffron Walden, The C. W. Daniel Company, Essex, England, 1980; 120-121.

Certain drugs commonly prescribed for urinary incontinence, such as oxybutynin hydrochloride, inhibit the muscarinic action of acetylcholine on smooth muscle, producing a direct antispasmodic action, that is, they relax the detrusor muscle. Tapp A. J. S. et al., Brit. J. Obstetrics and Gynecology,; 97: 521-6 (1990). This antispasmodic effect is desired over the anticholinergic effect of drugs previously used for patients with urinary incontinence. The antispasmodic effect of these essential oils, whilst not provided in more specific detail, may also be producing an action similar to currently prescribed drug medications.

Herbal diuretics are documented as increasing blood flow through the kidneys without resorption at the distal tubule of the nephron and associated loss of electrolytes (apart from potassium), as is the case with more sophisticated modern drug diuretics. Mills and Bone, *Principles and Practice of Phytotherapy*. Churchill Livingstone, 2000;35, 220-222. Also, diuresis often does not result from herbal diuretic use. Mills and Bone, *Principles and Practice of Phytotherapy*. Churchill Livingstone, 2000;35, 220-222. It may be that these herbal essential oils largely stimulate the blood flow to the kidneys resulting in an increase or greater efficiency in the production of urine. This effect, when combined with complete emptying of the bladder when voiding, may minimize the volume of urine lost through continual leakage.

Pharmaceutical Compositions and Formulations

The herb-containing compositions of the present invention can be used alone or further formulated with pharmaceutically acceptable compositions, vehicles, or adjuvants with a favorable delivery profile, i.e., suitable for delivery to a subject. Such compositions typically comprise the herb-containing composition of the invention and a pharmaceutically acceptable carrier. As used herein, "pharmaceutically acceptable carrier" is intended to include any and all solvents, dispersion media, coatings, antibacterial and antifungal compositions, isotonic and absorption delaying compositions, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. The use of such media and compositions for pharmaceutically active substances is well known in the art. Except insofar as any conventional media or composition is incompatible with the active composition, use thereof in the compositions is contemplated. Supplementary active compositions can also be incorporated into the compositions.

A pharmaceutical composition of the invention is formulated to be compatible with its intended route of administration. Examples of routes of administration include, e.g., oral; transdermal (i.e., topical), and transmucosal administration. The pH can be adjusted with acids or bases, such as hydrochloric acid or sodium hydroxide.

Oral compositions generally include an inert diluent or an edible carrier. They can be enclosed in gelatin capsules, caplets or compressed into tablets. For the purpose of oral therapeutic administration, the herb-containing composition of the invention can be incorporated with excipients and used in the form of tablets, troches, or capsules. Oral compositions can also be prepared using a fluid carrier for use as a mouthwash, wherein the composition in the fluid carrier is applied orally and swished and expectorated or swallowed. Pharmaceutically compatible binding compositions, and/or adjuvant materials can be included as part of the composition. The tablets, pills, capsules, troches and the like can contain any of the following ingredients, or compositions of a similar nature: a binder such as microcrystalline cellulose, gum tragacanth or gelatin; an excipient such as starch or lactose, a disintegrating composition such as alginic acid, Primogel, or corn starch; a lubricant such as magnesium stearate or Sterotes; a glidant such as colloidal silicon dioxide; a sweetening composition such as sucrose or saccharin; or a flavoring composition such as peppermint, methyl salicylate, or orange flavoring. The herb-containing compositions of the present invention can also be formulated as a topical cream for transdermal or transmucosal administration.

In one embodiment, the herb-containing compositions of the invention are prepared with carriers that will protect the composition against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

The pharmaceutical compositions can be included in a container, pack, or dispenser together with instructions for administration.

The invention is further defined by reference to the following examples, which are not meant to limit the scope of the present invention. It will be apparent to those skilled in the art that many modifications, both to the materials and methods, may be practiced without departing from the purpose and interest of the invention.

EXAMPLES

Example 1

Clinical Trial of a Herb-Containing Natural Therapeutic Cream for Urinary Incontinence General Studies were conducted to investigate the effectiveness of a herb-containing natural therapeutic bladder control cream in relieving urinary incontinence (hereinafter, "bladder control cream" or bladder control cream test preparation). The bladder control cream tested) was a natural herb-containing cream preparation. The test preparation contained primarily essential oil herbal actives, e.g., essential oils of Citrus sinensis (orange) oil, *Juniperus virginiana* (Virginia cedarwood) stem oil, Commiphora myrrha (Myrrh) oil, Citrus aurantium (Neroli or Orange flower) oil, and *Cupressus sempervirens* (Cypress) leaf, and was formulated in accordance with the principles of essential oil administration. Battaglia, S., In: The Complete Guide to Aromatherapy. The Perfect Potion Pty Ltd, Virginia, Brisbane, Qld, Australia, pp. 110-113; 116; 150-151; 158-159; 182-183; 184-185; 187 (1995); Chidell, L., In Aromatherapy. A Definitive Guide to Essential Oils. Hodder and Stoughton Ltd, Kent, UK, pp. 23-24; 80-81 (1992); Keller, E., In: The Complete Home Guide to Aromatherapy, H J Kramer, Inc, Tiburon, Calif., USA, pp.178-179 (1991).

Materials and Methods

Study Design

The study was conducted according to the TGA's "Guidelines for Good Clinical Research Practice (GCRP) in Australia". The study was approved by the Australian College of Natural Medicine Ethics Committee. The interviews were conducted at the Naturopathic Clinic at the Australian College of Natural Medicine, Brisbane. Thirteen (13) women experiencing symptoms of urge incontinence and/or stress incontinence were recruited through newspaper advertisements. Three (3) women withdrew from the study for personal reasons within the first few weeks. The remaining 10 women completed the three months of the study. Women experiencing urinary incontinence on a regular basis were considered eligible for inclusion in the study if they met the following criteria:

They had not undergone recent surgery particularly hysterectomy or prolapse repair (within the last 12 months);

They had not recently undergone childbirth (within the last 12 months);

They were not using any medicine for incontinence symptoms in the last month;

They did not have any serious health conditions such as diabetes mellitus, heart disease, pancreatic, hepatic disease or chronic inflammatory conditions;

They were not currently being treated for psychotic disturbances; and

They did not suffer from skin disorders that are affected by transdermal applications.

Women were asked to maintain current dietary patterns but were not given any advice regarding diet during the study. The exercise patterns of the participants were also noted, with women engaged in some form of exercise at least three times a week regarded as being active.

Participants were asked to apply five grams of the cream to the body twice daily for a period of three months. The effectiveness of the treatment was assessed using the short versions of the Incontinence Impact Questionnaire (IIQ) and the Urogenital Distress Inventory (UDI) prior to commencing treatment (month 0) and each month thereafter (months 1, 2 and 3). The short version (six questions) of the IIQ assesses the impact of incontinence on daily activities, such as household chores, physical activity and social activities. The questions in the UDI relate specifically to the physical aspects of incontinence. All questions are rated on a scale of 0 to 3 (0=not bothered, 1=slightly bothered, 2=moderately bothered, 3=extremely bothered). Both questionnaires are standardized disease specific questionnaires that provide efficient levels to detect bothersome incontinence in older people. Robinson, et al., Obstetrics and Gynecology, 91:2, 224-8 (1998). The results of these questionnaires were analyzed using the paired t-test.

Test Preparation

The bladder control cream test preparation was manufactured in accordance with the GMP guidelines by a TGA approved manufacturing site. Each gram of the bladder control. cream test preparation contained extracts equivalent dry 30 mg C. nurvala stem/bark extract; and 20 mg E. arvense (Horsetail) leaf; as well as the essential oils of 10 mg Orange oil; 500 μg J. virginiana (Cedarwood) stem; 500 μg Myrrh oil; 500 μg Orange flower oil; 100 μg C. sempervirens (Cypress) leaf; 5 mg d-alpha-tocopheryl acetate (Natural Vitamin E); 3.3 mg diazolidinylurea; and 1.54 mg total hydroxybenzoates. The essential oils used in this preparation are not known to be toxic, irritating or sensitizing.

Results and Discussion

Eight (8) of the women were aged between 60 and 78, with the other two women being significantly younger, 27 and 42 years. The body mass index (BMI) ranged from 24.4 to 31.9 with an average of 28.5. There was no change in weight in these women over the study period.

All women had given birth to at least one child, the average for the group being 2.0 children. All women had experienced symptoms of stress or urge incontinence for at least 10 years. Three (3) of the women had undergone surgery, either insertion of a sling or prolapse repair. None of the participants were using pelvic floor exercises prior to or during the study.

Prior to commencement of the treatment, all women reported that they were extremely bothered by leakage. The cause of the leakage was often a combination of the feeling of urgency, the result of physical activity or just continuous leakage. The results of the effectiveness of this treatment on the physical symptoms monthly over the study period are presented in Table 1 and FIG. 1.

TABLE 1

Urogenital Distress Inventory

| Do you experience, and if so, how much are you bothered by the following: | P values: month | | |
|---|---|---|---|
| | Month 1 | Month 2 | Month 3 |
| Frequent urination | 0.098 | 0.341 | 0.262 |
| Leakage due to feeling or urgency | 0.018 | 0.007 | 0.003 |
| Leakage due to activity, coughing, sneezing | 0.012 | 0.002 | 0.001 |
| Small amounts of leakage (drops) | 0.222 | 0.139 | 0.007 |
| Difficulty empting bladder | 0.254 | 0.339 | 0.041 |
| Pain or discomfort in lower abdominal or genital area | 0.500 | 0.500 | 0.500 | paired t-test p = <0.05

The study results indicated a significant positive change in the responses concerning leakage relating to urgency and activity. These effects were observed after the initial month on the treatment and continued to improve over the three months. There were also improvements in the area of continual leakage and difficulty emptying bladder, although these only became significant after the full three months of the treatment.

It is noteworthy, however, that there were no significant changes in the response to frequency of urination over the three months. None of the women were experiencing pain or discomfort in the lower abdomen or lower region, (responding as "not bothered" throughout the study) and did not suffer from frequent urinary tract infections (which is common amongst incontinence sufferers). There were no significant differences in the responses of the non-active group (n=5) compared to the active group (n=5) to the questions in the IIQ and UDI.

Most of the women reported that incontinence had a negative impact (by a "moderately bothered" or "severely bothered" response at month 0) on their lifestyle and social activities. Comparison of initial responses with those at month 3 showed significant positive changes in response to household chores, physical recreational activities and feeling frustrated (see Table 2).

TABLE 2

Incontinence impact questionnaire

| Has urine leakage affected the following: | Month 1 | Month 2 | Month 3 |
|---|---|---|---|
| Household chores | 0.039 | 0.039 | 0.006 |
| Physical recreation | 0.099 | 0.204 | 0.026 |
| Entertainment activities | 0.051 | 0.500 | 0.085 |
| Travel >30 min from home | 0.302 | 0.182 | 0.226 |

TABLE 2-continued

Incontinence impact questionnaire

| Has urine leakage affected the following: | Month 1 | Month 2 | Month 3 |
|---|---|---|---|
| Social activities | 0.178 | 0.500 | 0.098 |
| Emotional health | 0.500 | 0.182 | 0.091 |
| Feeling frustrated | 0.383 | 0.023 | 0.009 | paired t-test p = <0.05

There was a general, but not significant improvement in quality of life questions regarding social activity and emotional health due to incontinence over the three months. There were no significant changes in the responses regarding the impact of incontinence on entertainment activities or traveling 30 minutes from home during the study.

Previous studies demonstrated that incontinence has a negative impact on quality of life. Peake et al., Med Anthropol. Q, 13(3):267-85 (1999); Association for Continence Advice, Aust. Continence J.; 6(2):15-23 (2000); Robinson et al., Obstetrics and Gynecology, 91:2, 224-8 (1998). The present study indicated a significant improvement in the control of leakage (due to urgency and physical activity) and bladder emptying after three months of treatment with the bladder control cream test preparation. This effect was independent of diet and exercise patterns. It was also noteworthy that this positive response occurred in the absence of specific pelvic exercises.

These results indicated that improvement in physical symptoms was associated with improved self-confidence and ability to function on a daily basis. The formulation of the essential oils in the bladder control cream test preparation appeared to target the urinary system and promote better control over urination. The bladder control cream test preparation may act on the muscles of the pelvic floor, sphincter or bladder wall itself. The absorption of astringent essential oils of the bladder control cream test preparation may be minimal but may promote an antisecretory effect on mucous membranes or a 'toning' effect. Mills and Bone, In *Principles and Practice of Phytotherapy*. Churchill Livingstone, 35, pp. 220-222 (2000). In combination, the astringent and diuretic actions of the bladder control cream test preparation may produce a 'regulation' or 'normalization' of urine flow, improving control of urination, without producing diuresis.

A notable result in Table 1 was the dramatic decrease in "Leakage due to feeling or urgency." This significant positive change in the responses concerning urge incontinence ("OAB wet") indicates that the formulation may be useful for treating overactive bladder (OAB) in general. Both "OAB wet" and "OAB dry" are caused by the sudden, involuntary contraction of the muscle in the wall of the urinary bladder, which produce a sudden feeling or urgency to urinate.

Example 2

Clinical Trial of Herb-Containing Natural Therapeutic Tablet for Urinary Incontinence General Studies were conducted to investigate the effectiveness of a herb-containing natural therapeutic bladder control preparation in relieving urinary incontinence (hereinafter, "bladder control preparation" or "bladder control test preparation"). Steels, E., Seipel, T. and Rao, A., Australian Continence Journal (2002). The bladder control test preparation was a natural herb-containing preparation formulated as a tablet. Each tablet contained extracts equivalent dry: *C. nurvala* stem/bark extract (3,000 mg) 3 g, *E. arvense* (Horsetail) herb (1,500 mg) 1.5 g and Magnesium phosphate 70 mg, Calcium hydrogen phosphate 70 mg, equiv. Calcium 16.3 mg, Magnesium 14.5 mg, Phosphorous 24.9 mg. Contains maltodextrin.

Materials and Methods

Study Design

Eight (8) women experiencing symptoms of urge incontinence and/or stress incontinence on a regular basis were recruited through newspaper advertisements. All women met the following criteria:

(a) had not undergone recent surgery particularly hysterectomy or prolapse repair within the last 12 months,
(b) did not have any serious health conditions such as diabetes mellitus, heart disease, pancreatic disease, hepatic disease or chronic inflammatory conditions,
(c) were not currently being treated for psychotic disturbances, and
(d) did not use any medicine for incontinence symptoms in the last month prior to commencement of the study.

None of the participants were engaging in the specific pelvic exercises to improve muscle tone prior to the study, although they were aware of them.

The treatment protocol consisted of two tablets twice daily (equivalent to 12 g Crateva and 6 g *Equisetum* daily) over a period of 12 weeks. The efficacy of the treatment was assessed using the short versions of the Incontinence Impact Questionnaire (IIQ) and the Urogenital Distress Inventory (UDI) prior to commencing treatment (month 0) and each month thereafter (months 1, 2 and 3). The short version (six questions) of the IIQ assesses the impact of incontinence on daily activities, such as household chores, physical activity and social activities. The questions in the UDI relate specifically to the physical aspects of incontinence. All questions are rated on a scale of 0 to 3 (0=not bothered, 1=slightly bothered, 2=moderately bothered, 3=extremely bothered). Both questionnaires are standardized disease specific questionnaires used to detect bothersome incontinence in older people. Robinson, D. et al., Obstetrics and Gynecology, 91:2, 224-8 (1998).

The study group consisted of eight women. Seven of the participants were aged between 54 and 65, with one participant being 20 years of age. The average age of the study group was 50 years. Six of the participants had given birth to at least two children, while two participants had not had children. The results of these questionnaires were analyzed using the paired t-test.

Test Preparation

The bladder control test preparation tablets were manufactured in accordance with the GMP guidelines by a TGA approved manufacturing site. Each tablet contained the herbs, *C. nurvala* stem/bark extract and *E. arvense* leaf and the minerals, magnesium phosphate and calcium phosphate. The study was conducted according to the TGA's "Guidelines for Good Clinical Research Practice (GCRP) in Australia". The study was approved by the Australian College of Natural Medicine Ethics Committee. The interviews were conducted at the Naturopathic Clinic at the Australian College of Natural Medicine, Brisbane.

Results and Discussion

The effectiveness of the bladder control test preparation on the physical symptoms is summarized in Table 3 and FIG.

Figure 2:
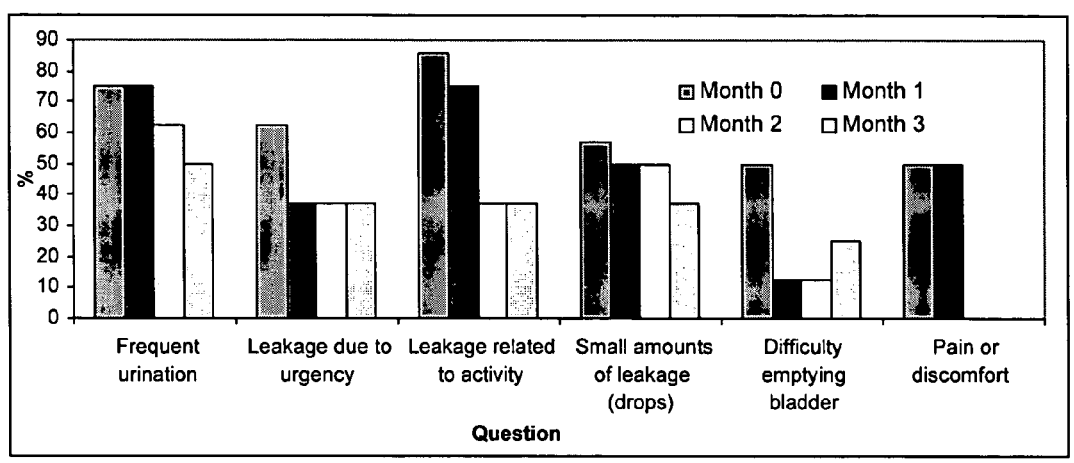
FIG. 2 is a histogram graph showing the percentage of "extremely bothered" responses during clinical assessment of an herb-based tablet to treat urinary incontinence.

2. Prior to treatment, 80% of the participants reported that they were bothered by leakage related to activity. This was reduced to 40% after 3 months of treatment (FIG. 2). Similar responses were observed for leakage due to urgency (60% to 35%), frequent urination reduced (70% to 48%), difficulty emptying bladder (50% to 25%). Prior to treatment, 50% of participants experienced pain or discomfort prior to treatment, but none reported these symptoms after 2 months of treatment. There was a 25% reduction in the number of women responding to small amounts of leakage (75% to 50%) after treatment.

Analysis (paired t-test) of the data showed that there was a significant positive change in the perceptions of frequency of urination after a month of treatment (p=0.040), and this continued in a gradual manner over the duration of the study (p=0.24 at 2 months, p=0.013 at 3 months). There was a significant positive change in perceptions regarding leakage relating to urgency (p=0.024), leakage due to activity (p=0.031), and difficulty emptying bladder (p=0.052) after 3 months of treatment. Again, positive effects were seen after the first initial month of treatment.

There was a positive trend in the responses regarding the small amounts of leakage during the study but these were not significant. A significant positive response in relation to pain or discomfort in the lower abdomen or lower region (p=0.025) was also observed after 2 months of treatment.

TABLE 3

Urogenital Distress Inventory

| Do you experience, and if so, how much are you bothered by: | Month 1 | Month 2 | Month 3 |
|---|---|---|---|
| Frequent urination | 0.040 | 0.024 | 0.013 |
| Leakage due to feeling or urgency | 0.052 | 0.024 | 0.024 |
| Leakage due to activity, coughing, sneezing | 0.086 | 0.009 | 0.031 |
| Small amounts of leakage (drops) | 0.178 | 0.145 | 0.091 |
| Difficulty empting bladder | 0.025 | 0.025 | 0.052 |
| Pain or discomfort in lower abdominal or genital area | 0.366 | 0.025 | 0.025 | paired t-test p = <0.05

Figure 3:
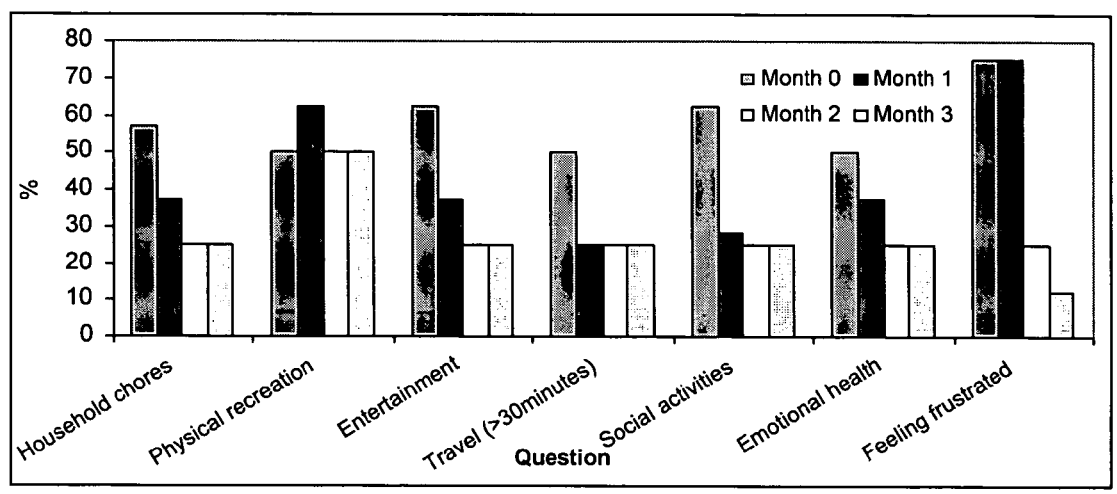
FIG. 3 is a histogram graph showing the percentage of "extremely bothered" responses during clinical assessment of an herb-based tablet to treat urinary incontinence.

The responses to the Incontinence Impact Questionnaire are presented in Table 6 and FIG. 3. The results showed that participants felt that incontinence had a significant negative impact on their quality of life, as assessed by a range of 50-70% "bothered score" for the seven parameters of the IIQ (FIG. 3). This was reduced significantly (to a range of 10-25%) for all parameters, except the question regarding physical recreation, in which there was little variation between month 0 and month 3.

Analysis (paired t-test) of the data showed that there was an improvement in the perception of the effect of incontinence on lifestyle and social activities, indicated by positive changes in response to social activities (p=0.04), entertainment activities (p=0.017), emotional health (p=0.025) and travel >30 minutes from home (p=0.052), feeling frustrated (p=0.007) after 3 months of treatment. There was no change in the responses regarding household chores or physical recreation (Table 4).

TABLE 4

Incontinence impact questionnaire

| Has urine leakage affected the following: | Month 1 | Month 2 | Month 3 |
|---|---|---|---|
| Household chores | 0.100 | 0.100 | 0.100 |
| Physical recreation | 0.299 | 0.302 | 0.229 |
| Entertainment activities | 0.175 | 0.040 | 0.017 |
| Travel >30 min from home | 0.040 | 0.052 | 0.052 |
| Social activities | 0.086 | 0.017 | 0.040 |
| Emotional health | 0.070 | 0.040 | 0.025 |
| Feeling frustrated | 0.017 | 0.019 | 0.007 | paired t-test p = <0.05

The results from this study indicate a significant (at p>0.05) improvement in the control of leakage (due to urgency and physical activity), bladder emptying and pain or discomfort after three months of treatment with the bladder control test preparation. These results are supported by reports of earlier studies showing that treatment with *Crateva* relieved incontinence, pain and retention of urine in men. Deshpande P. J. et al., Indian J. Med. Res., 76(Suppl): 46-53 (1982).

Acetylcholine is the primary excitatory neurotransmitter involved in bladder emptying. Certain drugs commonly prescribed for urinary incontinence, such as oxybutynin hydrochloride, inhibit the muscarinic action of acetylcholine on smooth muscle, producing a direct antispasmodic action. These drugs relax the detrusor muscle. Wada Y. et al., Arch. Int. Pharmacodyn. Ther., 330(1):76-89 (1995); Tapp A. J. S. et al., Brit. J. Obstetrics Gynecology, 97: 521-6 (1990). These medications also produce unwanted anticholinergic effects, such as dry mouth, blurred vision and constipation. Pathak A S, Aboseif S R. Overactive Bladder: Drug therapy versus nerve stimulation. Nat Clin Pract Urol, 2(7):310-311, 2005. There are currently no medications that specifically target incontinence symptoms without having side effects elsewhere in the body. The mechanisms whereby these herbal drugs exert these effects is unknown, although it is interesting to note that there were no side effects reported from the treatment, as seen with the anticholinergic drugs.

Example 3

Clinical Trial of an Herb-Containing Natural Therapeutic Tablet (Formula 2) with Standardized Silicon Content for Use in the Prevention and Treatment of Urinary Incontinence and Overactive Bladder (OAB)

General

Studies were conducted to investigate the effectiveness of an herb-containing natural therapeutic bladder control preparation in relieving urinary incontinence and overactive bladder (i.e., bladder control test preparation) for oral administration. These studies were designed and performed as generally described above in Example 2 and further detailed below. The bladder control test preparation was a natural herb-containing preparation formulated as a tablet.

Silicon has been identified as a contributor to the biological activity of *E. arvense* herb. Non-standardized preparations of *E. arvense* herb generally contain silicon from about 1.2% to about 6.9% silicon based on total dry weight of preparation. In one aspect of the present invention, it has been determined that batch variation in the silicon content of *E. arvense* herb preparations can have negative effects on the biological activity of the composition of the present invention. This problem has been resolved by the present invention by providing an *E. arvense* herb preparation with optimized, standardized silicon content. Accordingly, in one embodiment of the invention, the silicon content of the *E. arvense* herb preparation in the herb-containing preparation of the invention is standardized. The use of a standardized preparation *E. arvense* herb is advantageous because the inter-batch variation of silicon is reduced, thus the composition of the present invention yields more consistent preventative or therapeutic effect.

Materials and Methods

Test Preparation

The bladder control test preparation tablets are manufactured in accordance with the GMP guidelines by a TGA approved manufacturing site. Each tablet contains the herbs, *C. nurvala* stem/bark extract and *E. arvense* stem extract and the minerals, magnesium phosphate and calcium phosphate and silicon. For example, each tablet contains dry weight equivalents as follows: *C. nurvala* stem/bark extract (3,000 mg), *E. arvense* (Horsetail) stem extract preparation with a standardized silicon content of 3% based on the total dry weight of the *E. arvense* stem extract preparation (1,500 mg), colloidal anhydrous silica (50.3 mg), magnesium phosphate 70 mg, calcium hydrogen phosphate 70 mg, equiv. calcium 16.3 mg, magnesium 14.5 mg, phosphorous 24.9 mg. Each tablet contains 41.6 mg dry weight equivalents of total silicon per tablet. Each tablet contains some maltodextrin.

Study Design

Human subjects (males and females) experiencing symptoms of overactive bladder, urge incontinence and/or stress incontinence on a regular basis were recruited through newspaper advertisements. All human subjects met the following criteria:
(a) had not undergone recent surgery particularly hysterectomy or prolapse repair within the last 12 months,
(b) did not have any serious health conditions such as diabetes mellitus, heart disease, pancreatic disease or hepatic disease,
(c) did not use any medicine for incontinence symptoms in the last month prior to commencement of the study.

None of the participants were engaging in the specific pelvic exercises to improve muscle tone prior to the study.

The treatment protocol consisted of human test subjects ingesting two tablets of the bladder control test preparation twice daily over a period of 12 weeks. The efficacy of the treatment was assessed by recording average daily and nightly frequency of urination and the short versions of the Incontinence Impact Questionnaire (IIQ) and the Urogenital Distress Inventory (UDI) prior to commencing treatment (month 0) and each month thereafter (months 1, 2, and 3). The questions in the UDI related specifically to the physical aspects of incontinence as detailed below in Table 5.

TABLE 5

Urogenital Distress Inventory

Do you experience, and if so, how much are you bothered by:

Frequent urination
Leakage due to feeling or urgency
Leakage due to activity, coughing, sneezing
Small amounts of leakage (drops)
Difficulty empting bladder
Pain or discomfort in lower abdominal or genital area The short version (six questions) of the IIQ assessed the impact of incontinence on daily activities, such as household chores, physical activity and social activities as summarized below in Table 6.

TABLE 6

Incontinence impact questionnaire

Has urine leakage affected the following:

Household chores
Physical recreation
Entertainment activities
Travel >30 min from home
Social activities
Emotional health
Feeling frustrated All questions were rated on a scale of 0 to 3 (0=not bothered, 1=slightly bothered, 2=moderately bothered, 3=extremely bothered). Both questionnaires were standardized disease specific questionnaires used to detect bothersome incontinence in older people. Robinson, D. et al., Obstetrics and Gynecology, 91:2, 224-8 (1998). Also analyzed was the average frequency of urination during the day and night at month 0,1,2 and 3, these results were also compared using a paired t-test.

The results of these questionnaires were analyzed using the paired t-test. A positive improvement was defined as a statistically significant difference, i.e., $p$ value$\leq 0.05$, in a parameter measuring the physical aspects of incontinence or the physical or social activities of test subjects receiving the bladder control test preparation when compared to the same parameter in human test subjects prior to receiving the bladder control test preparation. A positive improvement in any parameter relating to the physical aspects of incontinence or the physical or social activities of human test subjects receiving the bladder control test preparation when compared to the same parameter in human test subjects prior to receiving the bladder control test preparation demonstrates that the bladder control test preparation is useful to prevent or treat a urogenital system disorder in a human subject, e.g., urinary incontinence; overactive bladder; enuresis; benign prostatic hyperplasia; urinary calculi; cystitis; and urinary tract infection.

Results and Discussion

Demographics

There were nine participants completing the study, three males and six females, with an average age of 52 years (range 41-72 years).

Frequency of Urination During The Day

The results show that the frequency of urination during the day reduced steadily during the 3 months of treatment. The number of times participants needed to empty the bladder reduced from 14 (prior to treatment), to 10 times per day (after 1 month), 8.3 times per day (after 2 months) and further reduced to 6.6 times per day by 3 months. This is shown to be a significant reduction between month 0 and subsequent months ($p=0.02$ at month 2; $p=0.01$ at month 3).

Frequency of Nocturia

The results show that this treatment was effective in reducing the number of times participants needed to empty the bladder at night. There was a gradual reduction in awakenings from 2.7 times per night initially to 2.0 times, 1.4 times and 1.0 times per night (month 1, 2 and 3 respectively). The results of the t-test showed there was a significant reduction in frequency between month 0 and month 2 (p=0.047) and month 3 (p=0.024).

The majority of participants in the study reported nocturia as a major symptom and one of the reasons for participating in this study. The overall improvement in Quality of Life (discussed below) appeared directly linked to the fact that they were experiencing longer periods of uninterrupted sleep (notes from individual files).

The Urogenital Distress Inventory

Figure 4:
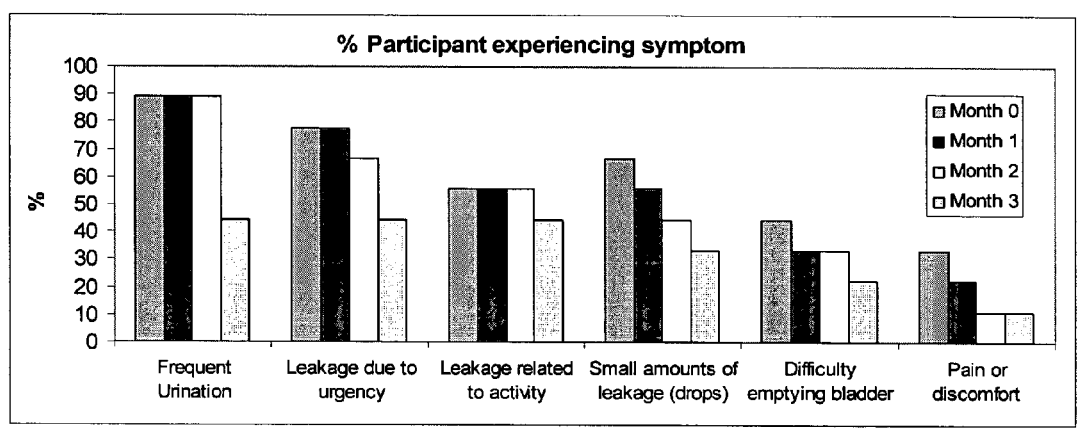
FIG. 4-FIG. 11 are histogram graphs showing the percentage of "bothered" responses during clinical assessments of an herb-based tablet to treat urinary incontinence and overactive bladder.
Figure 5:
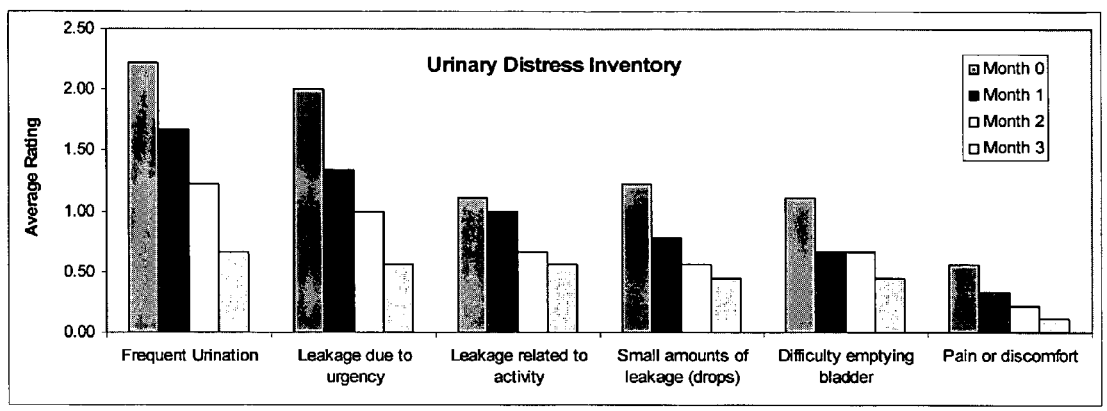

The symptoms experienced by most participants (FIG. 4) were: frequent urination, (approximately 89%). leakage due to urgency affecting 78% of the participants, and small amounts of leakage 67%. Other symptoms included leakage due to activity (56%), difficulty emptying bladder (44%) and pain or discomfort (33%). The results presented in FIG. 5, (as the average bothered responses) indicate that symptoms in all of the categories reduced after one month of treatment and continued to decrease over the next 2 months.

these activities within 4 weeks of treatment, with continual improvement reported throughout the rest of the study.

The results of the questionnaire were analyzed using the paired t-test. There was an improvement in the perception of the effect of incontinence on lifestyle and social activities, indicated by positive changes in response to all questions by the end of the study. Significant improvements in all questions occurred at month 2 (see Table 7). The significant positive effect for questions regarding emotional health and feeling frustrated indicate that the treatment is associated with improvements in quality of life.

Participants were also asked at the month 3 interview if the treatment had improved their Quality of Life. Overall, 67% reported an improvement in QOL. These results clearly indicate that there is a significant improvement in QOL for participants that experience relief or a reduction in the severity in the symptoms of urinary incontinence and OAB, including frequency, nocturia, urgency and bladder discomfort.

TABLE 7

Results of paired t-test (p values) Urinary Distress Inventory and Incontinence Impact Questionnaire Urinary Distress Inventory

| t-test results | Frequent Urination | Leakage due to urgency | Leakage related to activity | Small amounts of leakage (drops) | Difficulty emptying bladder | Pain or discomfort |
|---|---|---|---|---|---|---|
| Month 0 vs 1 | 0.051 | 0.050 | 0.347 | 0.104 | 0.035 | 0.169 |
| Month 0 vs 2 | 0.009 | 0.028 | 0.104 | 0.022 | 0.035 | 0.081 |
| Month 0 vs 3 | 0.011 | 0.016 | 0.139 | 0.043 | 0.081 | 0.225 |

Incontinence Impact Questionnaire

| T-test results | Household chores | Physical recreation | Entertainment activities | Travel greater than 30 min from home | Social activities | Emotional health | Feeling frustrated |
|---|---|---|---|---|---|---|---|
| Month 0 vs 1 | 0.195 | 0.195 | 0.051 | 0.272 | 0.051 | 0.104 | 0.195 |
| Month 0 vs 2 | 0.050 | 0.043 | 0.023 | 0.023 | 0.023 | 0.013 | 0.028 |
| Month 0 vs 3 | 0.052 | 0.052 | 0.023 | 0.021 | 0.023 | 0.007 | 0.016 |

The results of the questionnaire were analyzed using the paired t-test. A significant positive change in the frequency of urination occurred after 2 months and remained significant at month 3 of treatment (p=0.009, 0.011 respectively). Other significant reductions in symptoms occurred by month 2 and continued to be significant at month 3 were: leakage due to urgency (p=0.028, 0.016 respectively)., difficulty emptying bladder (p=0.035, 0.081 respectively), and small amounts of leakage (p=0.022, 0.043 respectively).

Incontinence Impact Questionnaire

Figure 6:
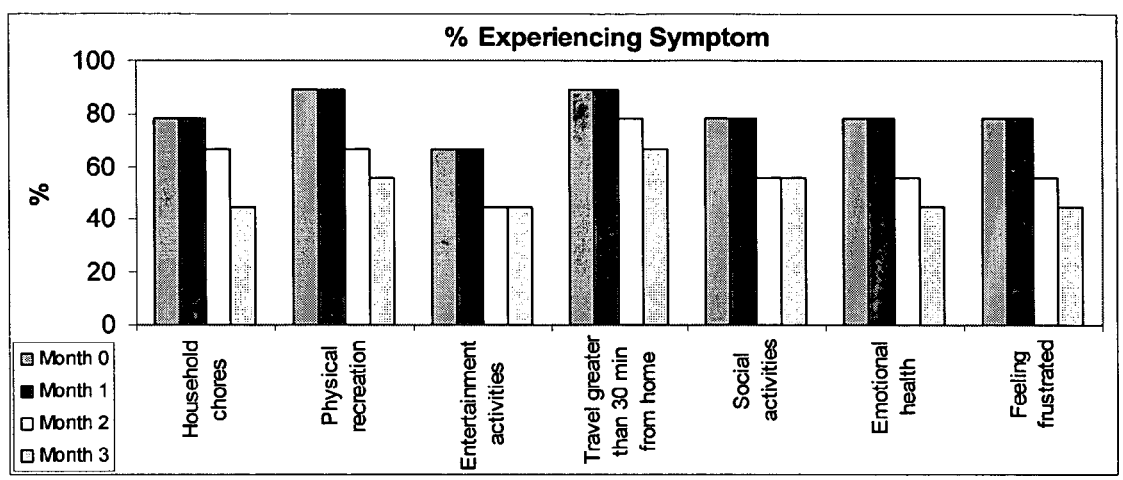

The activities that showed to be most impacted on by incontinence and OAB (FIG. 6) were: Physical recreation and Travel greater than 30 minutes from home (approximately 89%). Household chores, Social activities, Emotional health and Feeling frustrated were experienced by 78% of participants and Entertainment activities were affected in 67% of participants.

Figure 7:
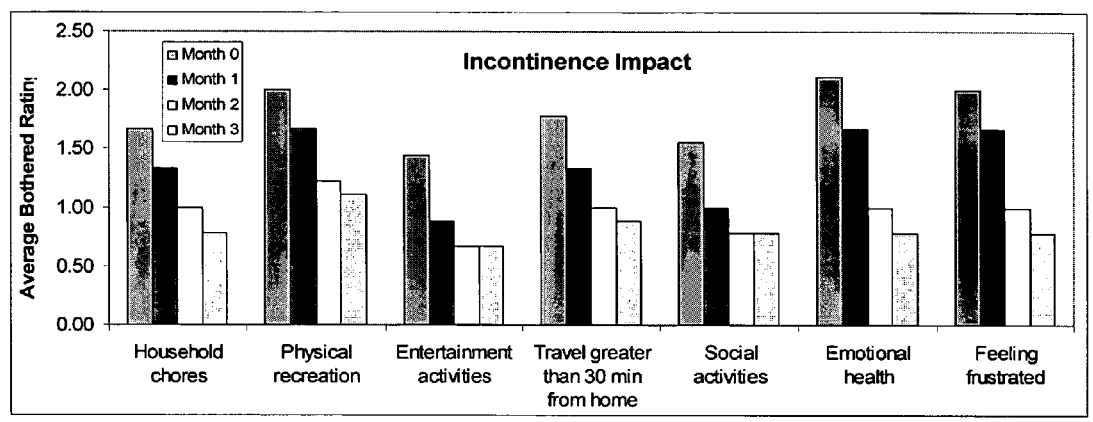

The results presented in FIG. 7, (as the average bothered responses) clearly show that quality of Life (assessed through difficulty in doing daily and social activities as well as emotional health and feelings of frustration) are adversely affected by having the symptoms of Incontinence. On average, participants were less bothered (and most confident) in

CONCLUSION

The results of this study indicate that Formula 2 preparation, using *E. arvense* standardized for silicon content, was a suitable and effective treatment for both men and women, It was effective in reducing symptoms of urinary incontinence and OAB, including frequency, nocturia, urgency and bladder discomfort. Symptom relief occurred after 4 weeks of treatment, with the severity of symptoms reducing further, especially in the 8-12 week period of using the treatment. The treatment was not associated with major adverse reactions.

Formula 2, with *E. arvense* standardised for silica content, showed comparable results to the original tablet formula, however results generally occurred faster with severity of symptoms (bothered rating) decreasing more consistently after 1 month of treatment. Also at month 3 of treatment, less participants were experiencing the urinary distress symptoms compared to month 3 results of Formula 1.

This study shows that Formula 2, containing *E. arvense* standardized for silica content, is more effective than a similar formula with no standardization for silicon.

Example 4

Clinical Trial of an Herb-Containing Natural Therapeutic Tablet with Standardized Silicon Content and Flavonoid Content (Formula 3) for Use in the Prevention and Treatment of Urinary Incontinence and Overactive Bladder (OAB).

General

Studies were conducted to investigate the effectiveness of an herb-containing natural therapeutic bladder control preparation in relieving urinary incontinence and OAB (i.e., bladder control test preparation) for oral administration. These studies were designed and performed as generally described above in Example 2 and Example 3 and further detailed below. The bladder control test preparation was a natural herb-containing preparation formulated as a tablet.

Silicon has been identified as a contributor to the biological activity of *E. arvense* herb. In addition to silicon, *E. arvense* contains about 5 percent of a saponin, designated equisetonin, and several flavone glycosides (a.k.a., flavonoids) including isoquercetrin, galuteolin, and equisetrin. Isoquercetrin (a.k.a, isoquercetin; Quercetin 3-O-β-D-glucopyranoside; 4H-1-Benzopyran-4-one, 2-(3,4-dihydroxyphenyl)-3-(β-D-glucofuranosyloxy)-5,7-dihydroxy-). Flavonoids, e.g., isoquercetrin, may have important pharmacological properties. In certain aspects of the present invention, it has been determined that batch variation in the silicon content and/or flavonoid content expressed as isoquercetrin of *E. arvense* herb preparations can have negative effects on the biological activity of the composition of the present invention. This problem has been resolved by the present invention by providing *E. arvense* herb preparations with optimized, standardized silicon content and flavonoid content expressed as isoquercetrin. The study assessed the efficacy of the improved formulation in preventing and treating the symptoms of urinary incontinence and OAB.

Materials and Methods

Test Preparation

The bladder control test preparation tablets were manufactured in accordance with the GMP guidelines by a TGA approved manufacturing site. Each tablet contained the herbs, *C. nurvala* stem/bark extract and *E. arvense* stem extract and the minerals, magnesium phosphate and calcium phosphate and silicon. For example, each tablet contained dry weight equivalents as follows: *C. nurvala* stem/bark extract (3,000 mg), *E. arvense* (Horsetail) stem extract preparation with a standardized silicon content of 3% and a standardized flavonoid content of 0.8% (expressed as isoquercetrin) based on the total dry weight of the *E. arvense* stem extract preparation (1,500 mg), colloidal anhydrous silica (50.3 mg), magnesium phosphate 70 mg, calcium hydrogen phosphate 70 mg, equiv. calcium 16.3 mg, magnesium 14.5 mg, phosphorous 24.9 mg. Each tablet contained 60.8 mg dry weight equivalents of total silicon per tablet. Each tablet contained some maltodextrin.

Study Design

Human subjects experiencing symptoms of urge incontinence and/or stress incontinence on a regular basis were recruited through newspaper advertisements. All human subjects met the following criteria:

(a) having not undergone recent surgery particularly hysterectomy or prolapse repair within the last 12 months, (b) did not have any serious health conditions such as diabetes mellitus, heart disease, pancreatic disease, or hepatic disease, (c) did not use any medicine for incontinence symptoms in the last month prior to commencement of the study.

None of the participants were engaging in the specific pelvic exercises to improve muscle tone prior to the study.

The treatment protocol consisted of human test subjects ingesting two tablets of the bladder control test preparation twice daily over a period of 12 weeks. The efficacy of the treatment was assessed by recording average daily and nightly frequency of urination and using the short versions of the Incontinence Impact Questionnaire (IIQ) and the Urogenital Distress Inventory (UDI) prior to commencing treatment (month 0) and each month thereafter (months 1, 2, and 3). The questions in the UDI related specifically to the physical aspects of incontinence as detailed below in Table 8.

TABLE 8

Urogenital Distress Inventory

Do you experience, and if so, how much are you bothered by:

Frequent urination
Leakage due to feeling or urgency
Leakage due to activity, coughing, sneezing
Small amounts of leakage (drops)
Difficulty empting bladder
Pain or discomfort in lower abdominal or genital area The short version (six questions) of the IIQ assesses the impact of incontinence on daily activities, such as household chores, physical activity and social activities as summarized below in Table 9.

TABLE 9

Incontinence impact questionnaire

Has urine leakage affected the following:

Household chores
Physical recreation
Entertainment activities
Travel >30 min from home
Social activities
Emotional health
Feeling frustrated All questions were rated on a scale of 0 to 3 (0=not bothered, 1=slightly bothered, 2=moderately bothered, 3=extremely bothered). Both questionnaires were standardized disease specific questionnaires used to detect bothersome incontinence in older people. Robinson, D. et al., Obstetrics and Gynecology, 91:2, 224-8 (1998). Also analyzed was the average frequency of urination during the day and night at month 0, 1, 2 and 3, these results were also compared using a paired t-test.

The results of these questionnaires were analyzed using the paired t-test. A positive improvement was defined as a statistically significant difference, i.e., p value ≦0.05, in a parameter measuring the physical aspects of incontinence or the physical or social activities of test subjects receiving the bladder control test preparation when compared to the same parameter in human test subjects prior to receiving the bladder control test preparation. A positive improvement in any parameter relating to the physical aspects of incontinence or the physical or social activities of human test subjects receiving the bladder control test preparation when compared to the same parameter in human test subjects prior to receiving the bladder control test preparation demonstrates that the bladder control test preparation is useful to prevent or treat a urogenital system disorder in a human subject, e.g., urinary incontinence; overactive bladder; enuresis; benign prostatic hyperplasia; urinary calculi; cystitis; and urinary tract infection.

Results and Discussion

Demographics

There were 10 participants (two males and eight women) completing the study with an average age of 65.9 years (range 49-71 years).

Frequency of Urination During The Day

The results demonstrated that the average frequency of urination during the day reduced significantly (p<0.05) during the 3 months of treatment. The number of times participants needed to empty the bladder reduced from 11.5 (prior to treatment), to 8.5 times per day (after 1 month), 6.6 times per day (after 2 months) and further reduced to 6.0 times per day by 3 months. These results were significant at month 1 (p=0.017) and remained significant throughout the study (p=0.02 at month 2 and month 3).

Frequency of Nocturia

The results demonstrated that this treatment was effective in reducing the number of times participants needed to empty the bladder at night. There was a reduction in awakenings from 2.5 times per night initially to 1.5 times, 0.5 times and 0.5 times per night (month 1, 2, and 3 respectively). This was a significant difference (p<0.05) at month 2 and 3 of treatment. Many of the participants were able to sleep though the night altogether after 2 months of treatment. These results were significant at month 1 (p=0.063) and remained significant throughout the study (p=0.007 at month 2; p=0.03 month 3).

The Urogenital Distress Inventory

Figure 8:
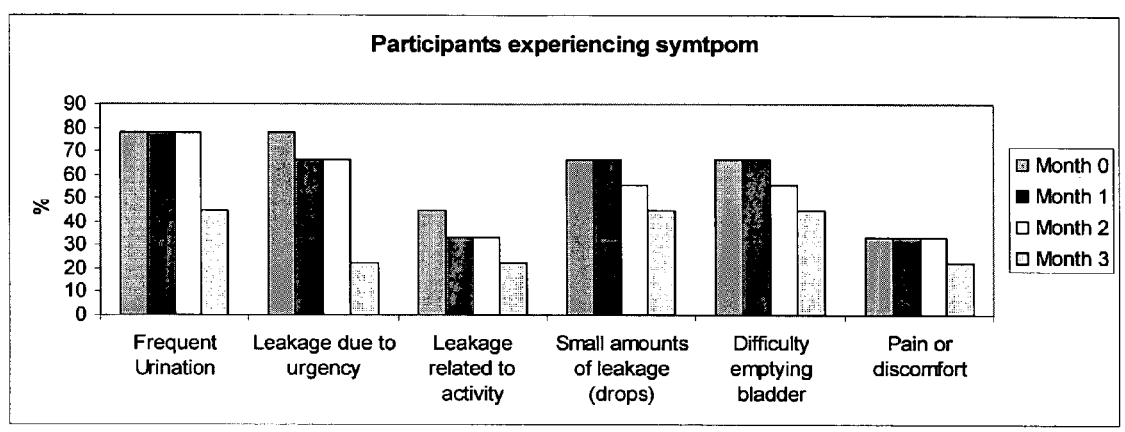
Figure 9:
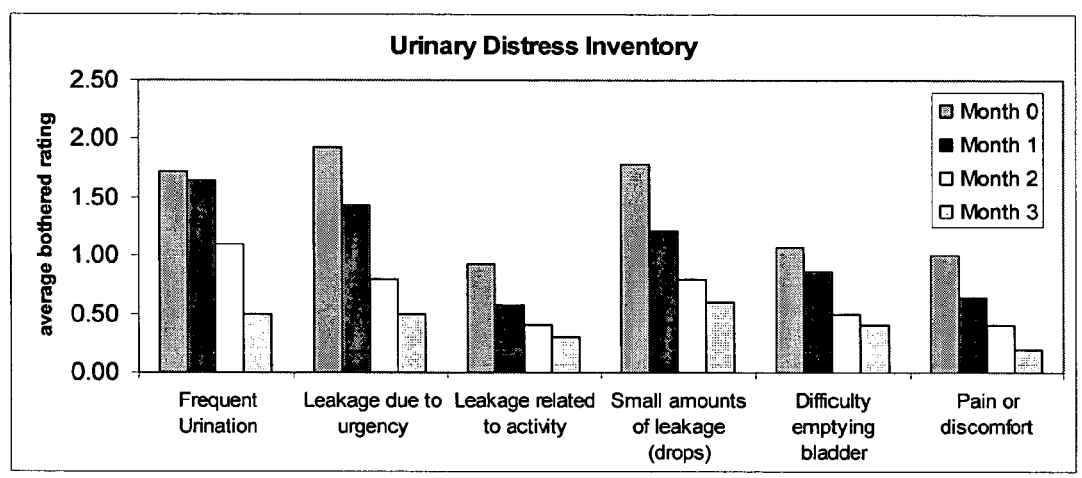

Symptoms experienced by most participants (FIG. 8) were: frequent urination (78%), urgency (78%), small amounts of leakage (67%), and emptying bladder (67%). The other symptoms were reported as less of a problem, were: leakage due to activity affecting 44% of the participants, with only 33% reporting pain in the abdominal region. The results presented in FIG. 9, (as the average bothered rating) indicate that all symptoms were reduced one month of treatment and continued to reduce over the next 2 months.

The results of the questionnaire were analyzed using the paired t-test. There was a significant positive change after 2 months of treatment which continued at month 3 for the following symptoms: a feeling of being less bothered by leakage due to urgency (p =0.011, 0.017 respectively), small amounts of leakage (p=0.011, 0.015 respectively), and difficulty in empting bladder (p=0.024, 0.045 respectively). A significant positive change in the frequency of urination occurred after month 3 (p=0.009).

Incontinence Impact Questionnaire

Figure 10:
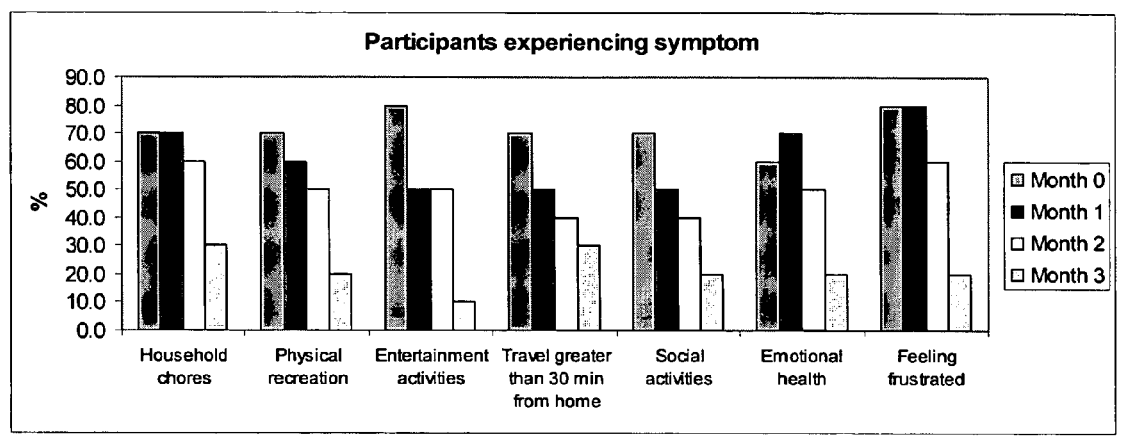

The activities that showed to be most impacted on by incontinence and OAB (FIG. 10) were: Entertainment activities and feeling frustrated (80%), physical recreation, and travel greater than 30 minutes from home, household chores, and social activities were experienced by 70% of participants and emotional health was affected in 60% of participants.

Figure 11:
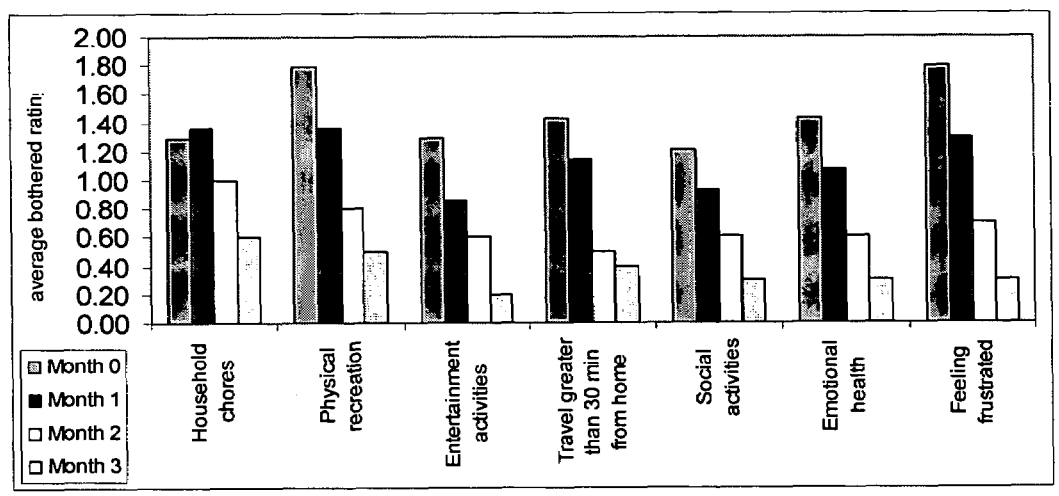

The results presented in FIG. 11, as the average bothered responses, clearly show that Quality of Life (assessed through difficulty in doing daily and social activities as well as emotional health and feelings of frustration) are adversely affected by having the symptoms of Incontinence. Participants were less bothered in most of these activities within 1 month of treatment, except for household chores (which reduced bothered rating at month 2) with continual improvement reported throughout the rest of the study.

The results of the questionnaire were analyzed using the paired t-test (Table 10). There was an improvement in the perception of the effect of incontinence on lifestyle and social activities, indicated by positive changes in response to all questions (except household chores) by the end of the study. Significant improvements in travel greater than 30 min were reported after the first month of treatment, with further positive effects observed at month 2 and month 3 (p=0.037, 0.010 and 0.015 respectively). After 2 and 3 months of treatment, there was a significant improvement in confidence in emotional health (p=0.081 and 0.029, respectively), and feeling frustrated (p=0.001 and 0.001, respectively), entertainment (p=0.015 and 0.004, respectively), and physical recreation (p=0.022 and 0.012, respectively), which indicates that the treatment is associated with improvements in quality of life.

Participants were also asked, at the month 3 interview, if the treatment had improved their Quality of Life. Overall, 70% reported an improvement in QOL These results clearly indicate that there is a significant improvement in QOL for participants that experience relief or a reduction in the severity in the symptoms of urinary incontinence and OAB, including frequency, nocturia, urgency and bladder discomfort.

TABLE 10

Results of paired t-test (p values) Urinary Distress Inventory and Incontinence Impact Questionnaire

| T-test results | Urinary Distress Inventory | | | | | |
|---|---|---|---|---|---|---|
| | Frequent Urination | Leakage due to urgency | Leakage related to activity | Small amounts of leakage (drops) | Difficulty emptying bladder | Pain or discomfort |
| Month 0 vs 1 | 0.591 | 0.096 | 0.168 | 0.015 | 0.168 | 0.081 |
| Month 0 vs 2 | 0.051 | 0.011 | 0.081 | 0.011 | 0.024 | 0.096 |
| Month 0 vs 3 | 0.009 | 0.017 | 0.269 | 0.015 | 0.045 | 0.089 |

TABLE 10-continued

Results of paired t-test (p values) Urinary Distress Inventory and Incontinence Impact Questionnaire

| T-test results | Incontinence Impact Questionnaire | | | | | | |
|---|---|---|---|---|---|---|---|
| | Household chores | Physical recreation | Entertainment activities | Travel greater than 30 min from home | Social activities | Emotional health | Feeling frustrated |
| Month 0 vs 1 | 0.726 | 0.081 | 0.104 | 0.037 | 0.193 | 0.509 | 0.104 |
| Month 0 vs 2 | 0.343 | 0.022 | 0.015 | 0.010 | 0.052 | 0.081 | 0.001 |
| Month 0 vs 3 | 0.132 | 0.012 | 0.004 | 0.015 | 0.011 | 0.029 | 0.001 |

CONCLUSION

The results of this study indicate that Formula 3, containing *E. arvense* standardised for silica and flavonoid content, was effective in reducing all symptoms of urinary incontinence and OAB, including frequency, nocturia, urgency and bladder discomfort. Symptom relief occurred after 4 weeks of treatment, with the severity of symptoms reducing further, especially in the 4-8 week period of using treatment. Formula 3 was suitable and effective treatment for both men and women and was not associated with major adverse reactions.

Accordingly, Formula 3 used in this study, demonstrated superior results to both Formula 1 and Formula 2. Formula 3 demonstrated increased effectiveness in reducing all symptoms of urinary incontinence and OAB and results were experienced within a shorter timeframe. This study demonstrated that Formula 3, containing *E. arvense* standardised for silica and flavonoid content is more effective than both Formula 1 and Formula 2.

Example 5

Comparison. of the Effectiveness of the Different Tablet Formulations (Formulations 1, 2 and 3) for Use in the Prevention and Treatment of Urinary Incontinence and Overactive Bladder (OAB)

General

The aim of this study was to compare the efficacy of three of the tablet formulations of the present invention, Formula 1, Formula 2 and Formula 3, in treating the symptoms of urinary incontinence and OAB by analysing the results of the Incontinence Impact Questionnaire (IIQ) and the Urogenital Distress Inventory (UDI) from each of the studies. Formula 1 is a non-standardized formula assessed in Clinical study Example 2; Formula 2 uses an *E. arvense* extract standardized for silicon and was assessed in Clinical study Example 3; and Formula 3 uses an *E. arvense* extract standardized for silicon and flavonoid content and was assessed in Clinical study Example 4.

Study Design

In order to directly compare the effectiveness of the three different tablet formulations, percent (%) reduction in bothered ratings for both questionnaires were compared. This method of analysis was used for comparison as month 0 (baseline) values in each of the studies varied. The frequency of urination and nocturia were directly assessed in Formula 2 and Formula 3 only.

Results and Discussion

The results from the Urinary Distress Inventory (UDI) indicate that Formula 2 (standardized for silicon content) had a higher effectiveness compared to Formula 1, specifically in the areas of frequent urination, leakage due to feeling of urgency, small amounts of leakage (drops) and difficulty empting bladder.

Formula 3 (standardized for Silicon and flavonoid content) was shown to be the most effective in reducing urinary distress (UDI), specifically frequent urination, leakage due to feeling or urgency, leakage due to activity, coughing, sneezing, small amounts of leakage (drops) and difficulty empting bladder by showing a higher percent reduction in symptom severity (Table 11). All formulations showed at least 75% effectiveness in reducing abdominal pain. However, since less than 40% of participants experienced this symptom at month 0, the results are not considered to be significant.

TABLE 11

Percent reduction in bothered rating of UDI for Formula 1, 2 and 3 at month 3

| | Formula 1 | Formula 2 | Formula 3 |
|---|---|---|---|
| Frequent Urination | 56 | 70 | 71 |
| Leakage due to urgency | 55 | 72 | 74 |
| Leakage related to activity | 64 | 50 | 68 |
| Small amounts of leakage (drops) | 61 | 64 | 66 |
| Difficulty in emptying bladder | 57 | 60 | 63 |

Comparison of the Incontinence Impact Questionnaire (IIQ) also indicated that Formula 3 had a better response (shown by reduction in symptoms) to all the QOL questions than Formula 1 and 2.

Figure 12:
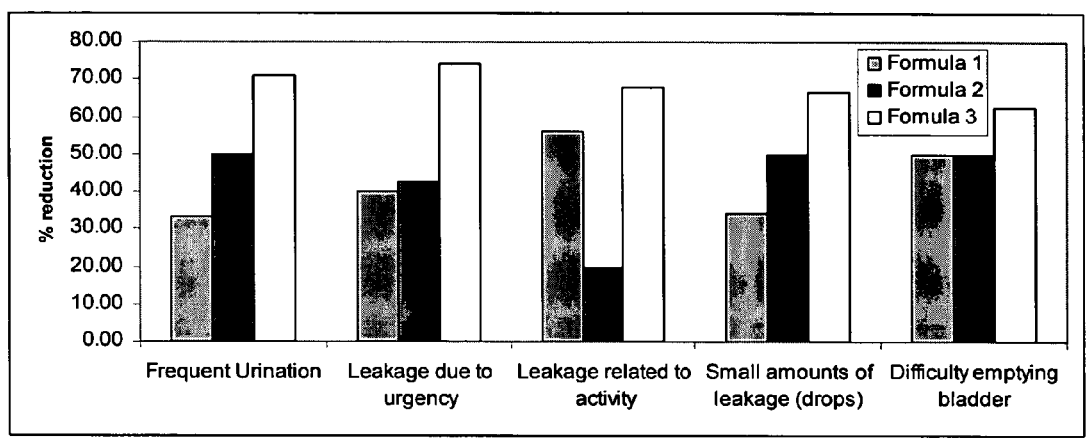
FIG. 12 is a histogram graph showing the percent reduction of people experiencing the symptoms of urinary incontinence and overactive bladder after three months of various herb-based tablet treatments.

The number (%) of people experiencing the symptoms at each month was also assessed. The Formula 3 showed increased effectiveness, in that there were less participants experiencing each symptom by 3 months, compared to the previous formulations (FIG. 12).

The frequency of urination and nocturia was only assessed in Formula 2 and Formula 3. Comparison of these results indicate that while both formulations were effective in reducing the frequency of urination during the day (by approximately 50%) and the effect was seen by the end of the first 8 weeks of treatment. However, Formula 3 was superior to Formula 2 in reducing nocturia with a 96% reduction in symptoms being observed by month 2 and overall a greater reduction in frequency (96% compared to 63% at month 3) (Table 12).

TABLE 12

Percent Decrease in Frequency of Urination

| | Day | | Night | |
|---|---|---|---|---|
| | Formula 2 | Formula 3 | Formula 2 | Formula 3 |
| Month 0 vs Month 1 | 28 | 26 | 35 | 40 |
| Month 0 vs Month 2 | 41 | 45 | 48 | 96 |
| Month 0 vs Month 3 | 53 | 48 | 63 | 96 |

CONCLUSION

The results of this study indicate that all preparations are safe and were not associated with major adverse reactions. All preparations were effective in reducing all symptoms of urinary incontinence and OAB, including frequency, nocturia, urgency and bladder discomfort. All preparations were shown to give symptom relief with the severity of symptom reduction generally being faster and more marked with Formula 2 and Formula 3. Formula 3 was the most effective compared with Formula 2 in reducing nocturia.

In summary, all formulations show effectiveness in treating symptoms of urinary incontinence and OAB. The standardization of the *E. arvense* for silicon (Formula 2) improved the effectiveness of the original formulation and this was further optimized by standardization of *E. arvense* for both Silicon and flavonoids (Formula 3).

Example 6

Silicon Testing of Formulations Used in Incontinence and Overactive Bladder Trials General Inter-batch variation of silicon content is expected in therapeutic formulations as many excipients contain silicon dioxide, in what is considered a non-absorbable form.

It has been suggested that inter-batch variation in silicon content of the formulations used in the incontinence and overactive bladder trials can result in the level of silicon falling below the therapeutically active silicon level per tablet.

The Formula 1 used in Clinical study Example 2 produced therapeutic effectiveness in relief from symptoms of urinary incontinence. As this formula used a non-standardized *Equisetum arvense* extract, inter-batch variation in silicon content of this formula is likely and may result in inconsistent effectiveness.

Formula 2 (used in Clinical study Example 3) and Formula 3 (used in Clinical study Example 4) were invented to resolve this problem of potential inter-batch variation and subsequent inconsistent effectiveness. They included an *E. arvense* extract standardized for silicon content and a consistent quantity of added colloidal anhydrous silica. The testing of all three formulations for silicon content was undertaken to determine the degree of possible inter-batch variation of Formula 1 and to confirm that therapeutic levels of silicon are maintained when using formulations containing *E. arvense* with standardized silicon content.

Various testing methods for measuring silicon content are available and may produce variable results. Therefore the same test method was used for each sample. The ICPMS test method currently listed in the British Pharmacopeia (BP) was used. This method completely destroys all other molecules in a composition, leaving only the silicon which can then be measured against a $SiO_2$ (silicon dioxide) control. This method measures all silicon and does not differentiate between bioavailable and non-absorbable forms of silicon.

Results

Formula 1, contains a non-standardized *E. arvense* extract. Upon testing, this batch of Formula 1 showed a silicon content of 34.0 mg per tablet (each tablet was approximately 1,000 mg). A subsequent batch of Formula 1 was tested for silicon content and showed 14.5 mg per tablet (again, each tablet was approximately 1,000 mg). This is an inter-batch variation of approximately 60% and highlights that when using a Horsetail extract that is not standardized for silicon that significant inter-batch variation in silicon content does occur. Inter-batch silicon content variation of this magnitude, and where the content falls below that shown to be effective in earlier research, is expected to reduce therapeutic effectiveness.

This was observed with the subsequent batch of Formula 1 containing 14.5 mg of silicon per tablet. This batch produced poorer and inconsistent results when compared to the original production batch of Formula 1 containing 34.0 mg silicon per tablet. (Data not shown)

Formula 2 and Formula 3 both use an *E. arvense* extract standardized for silicon and a consistent quantity of colloidal anhydrous silica. On testing, Formula 2 and 3 showed a silicon content per tablet of 41.6 mg and 60.8 mg per tablet, respectively (again, each tablet was approximately 1,000 mg). These levels were above the 34.0 mg silicon per tablet, shown in Clinical study Example 2 to be therapeutically effective. As well the variation in silicon content between batches of these two formulations was only 30%, a 50% reduction of the inter-batch variation of Formula 1. It would be expected that inter-batch variation (where the same formula (either Formula 2 or Formula 3) were used) would be minimized even further using these formulations with *E. arvense* standardized for silicon.

TABLE 13

Results of Silicon testing using ICPMS BP Method

| Formula | Description of Formula | Total Silicon (mg/tablet) | Total % Silicon (1000 mg tablet) |
|---|---|---|---|
| 1 | Original formula; original production batch Tested in Clinical study described in Example 2 | 34.0 | 3.40 |
| 1 | Original formula, subsequent batch | 14.5 | 1.45 |
| 2 | Improved formula - with standardized Silicon content Tested in Clinical study described in Example 3 | 41.6 | 4.16 |
| 3 | Improved formula with standardized Silicon content Tested in Clinical study described in Example 4 | 60.8 | 6.08 |

It should be noted that total % silicon described in Table 13 includes both bioavailable silicon from the standardized *Equisetum arvense* extract preparation and silicon from the excipients, which are largely non-bioavailable. The components of a tablet of Formula 2 are summarized in Table 14. According to the present invention, consistent good results are obtained with formulation with standardized *Equisetum arvense* extract preparation with at least about 3% silicon. In a preferred embodiment, the formulation includes a standardized *Equisetum arvense* extract preparation with at least about 3% to about 13% silicon. In another preferred embodiment, the formulation includes a standardized *Equisetum arvense* extract preparation with at least about 5% to about 10% silicon. In yet another preferred embodiment, the formulation includes a standardized *Equisetum arvense* extract preparation with at least about 6% silicon.

TABLE 14

Composition of a Formula 2 tablet

| Ingredients | Quantity (mg) | Estimated silicon contribution (mg) |
| --- | --- | --- |
| *C. nurvala* (10:1) | 300 | Nil |
| *E. arvense* (5:1, 3% Si) | 300 | 9 |
| Ca phosphate | 70 | Nil |
| Mg phosphate | 70 | Nil |
| Colloidal anhydrous Si | 50.32 | 23.5 |
| Fillers | 209.68 | 9.1 (approx) |
| Total: | 1,000 | 41.6 |

CONCLUSION

A consistent preventative or therapeutic effect would be more likely if inter-batch content of silicon in the tested formulae were minimized. The results of testing of different batches of a non-standardized silicon-containing formula (i.e., Formula 1) show inter-batch variation of 60%. Such batch variations are expected to result in inconsistent and reduced preventative and therapeutic effectiveness.

Formula 2 and Formula 3 use *E. arvense* extracts with standardized silicon contents and a consistent quantity of colloidal anhydrous silica, so consistent silicon content per tablet for each formula are obtained. The variation in silicon content between batches of these two formulations was only 30%, a 50% reduction of the inter-batch variation of Formula 1. It would be expected that inter-batch variation using the same formula (either 2 or 3) would be minimized even further.

By the use of a consistent optimal quantity of standardized silicon content of *E. arvense*, the bioavailable silicon content of the invention can be standardized per tablet. This avoids negative issues associated with batch variation in bioavailable silicon content.

The invention of Formula 2 and Formula 3, with an optimized, standardized silicon content of *E. arvense*, minimizes the problem of inter-batch variation in silicon content of formulations. Subsequently a more consistent preventive or therapeutic effect results, as shown in Clinical studies 3, 4 and 5.

EQUIVALENTS

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

I claim:

1. An herb-containing composition comprising a *Crateva nurvala* stem/bark preparation, a standardized *Equisetum arvense* stem extract preparation, and anhydrous colloidal silica, wherein the *Equisetum arvense* stem extract preparation has been standardized to have a silicon content from about 3% to about 13% silicon based on the total dry weight of the *Equisetum arvense* stem extract preparation, wherein the herb-containing composition is formulated as an oral dosage unit, and wherein the total silicon content of the herb-containing composition is from about 10 mg dry weight equivalents to about 71 mg dry weight equivalents per oral dosage unit.

2. The herb-containing composition of claim 1, wherein the *Crateva nurvala* stem/bark preparation is present at a concentration from about 2,500 mg to about 3,500 mg dry weight equivalents per oral dosage unit.

3. The herb-containing composition of claim 1, wherein the standardized *Equisetum arvense* stem extract preparation is present at a concentration from about 1,300 mg to about 1,600 mg dry weight equivalents per oral dosage unit.

4. The herb-containing composition of claim 1, further comprising anhydrous colloidal silica, wherein the total silicon content of the herb-containing composition is from about 28 mg dry weight equivalents to about 34 mg dry weight equivalents per oral dosage unit.

5. The herb-containing composition of claim 1, further comprising phosphorus, wherein the phosphorus is present at a concentration from about 5 mg dry weight equivalents to about 60 mg dry weight equivalents per oral dosage unit.

6. The herb-containing composition of claim 1, further comprising calcium, wherein the calcium is present at a concentration from about 1 mg dry weight equivalents to about 30 mg dry weight equivalents per oral dosage unit.

7. The herb-containing composition of claim 1, further comprising magnesium, wherein the magnesium is present at a concentration from about 1 mg dry weight equivalents to about 30 mg dry weight equivalents per oral dosage unit.

8. The herb-containing composition of claim 1, wherein the herb-containing composition is formulated in a dry delivery system.

9. The herb-containing composition of claim 1, wherein the herb-containing composition is formulated in a liquid delivery system.

10. The herb-containing composition of claim 1, wherein the herb-containing composition is formulated in a controlled-release vehicle.

11. The herb-containing composition of claim 1, wherein the oral dosage unit is selected from the group consisting of: a tablet; dry powder; capsule; and caplet.

12. A pharmaceutical composition comprising the herb-containing composition of claim 1 and a pharmaceutically-acceptable carrier.

13. An herb-containing composition, comprising: (a) a *Crateva nurvala* stem/bark preparation present at a concentration at least about 3,000 mg dry weight equivalents per oral dosage unit; (b) a standardized *Equisetum arvense* stem extract preparation with a silicon content at least about 3% silicon based on total dry weight of the *Equisetum arvense* stem extract preparation, wherein the standardized *Equisetum arvense* stem extract preparation is present at a concentration of at least about 1,500 mg dry weight equivalents per oral dosage unit; (c) a total silicon concentration of at least about 32.5 mg dry weight equivalents per oral dosage unit; (d) a phosphorus concentration of at least about 24.9 mg dry weight equivalents per oral dosage unit; (e) a magnesium concentration of at least about 14.5 mg dry weight equivalents per oral dosage unit; (f) a calcium concentration of at least about 16.3 mg dry weight equivalents per oral dosage unit; and wherein the herb-containing composition is formulated as an oral dosage unit.

14. The herb-containing composition of claim 13, wherein the herb-containing composition is formulated in a dry delivery system.

15. The herb-containing composition of claim 13, wherein the herb-containing composition is formulated in a liquid delivery system.

16. The herb-containing composition of claim 13, wherein the herb-containing composition is formulated in a controlled-release vehicle.

17. The herb-containing composition of claim 13, wherein the oral dosage unit is selected from the group consisting of: a tablet; dry powder; capsule; and caplet.

18. A pharmaceutical composition comprising the herb-containing composition of claim 13 and a pharmaceutically-acceptable carrier.

19. An herb-containing composition comprising a *Crateva nurvala* stem/bark preparation, a standardized *Equisetum arvense* stem extract preparation, and anhydrous colloidal silica, wherein the *Equisetum arvense* stem extract preparation has been standardized to have a silicon content from about 3% to about 13% silicon and a total flavonoid content from about 0.01% to about 3% total flavonoids based on the total dry weight of the *Equisetum arvense* stem extract preparation, wherein the total flavonoid content is expressed as isoquercetin, wherein the herb-containing composition is formulated as an oral dosage unit, and wherein the total silicon content of the herb-containing composition is from about 10 mg dry weight equivalents to about 71 mg dry weight equivalents per oral dosage unit.

20. The herb-containing composition of claim 19, wherein the *Crateva nurvala* stem/bark preparation is present at a concentration from about 2,500 mg to about 3,500 mg dry weight equivalents per oral dosage unit.

21. The herb-containing composition of claim 19, wherein the standardized *Equisetum arvense* stem extract preparation is present at a concentration from about 1,300 mg to about 1,600 mg dry weight equivalents per oral dosage unit.

22. The herb-containing composition of claim 19, further comprising anhydrous colloidal silica, wherein the total silicon content of the herb-containing composition is from about 28 mg dry weight equivalents to about 34 mg dry weight equivalents per oral dosage unit.

23. The herb-containing composition of claim 19, further comprising phosphorous, wherein the phosphorous is present at a concentration from about 5 mg dry weight equivalents to about 60 mg dry weight equivalents per oral dosage unit.

24. The herb-containing composition of claim 19, further comprising calcium, wherein the calcium is present at a concentration from about 1 mg dry weight equivalents to about 30 mg dry weight equivalents per oral dosage unit.

25. The herb-containing composition of claim 19, further comprising magnesium, wherein the magnesium is present at a concentration from about 1 mg dry weight equivalents to about 30 mg dry weight equivalents per oral dosage unit.

26. The herb-containing composition of claim 19, wherein the herb-containing composition is formulated in a dry delivery system.

27. The herb-containing composition of claim 19, wherein the herb-containing composition is formulated in a liquid delivery system.

28. The herb-containing composition of claim 19, wherein the herb-containing composition is formulated in a controlled-release vehicle.

29. The herb-containing composition of claim 19, wherein the oral dosage unit is selected from the group consisting of: a tablet; dry powder; capsule; and caplet.

* * * * *